United States Patent
Kusens et al.

(10) Patent No.: US 10,090,068 B2
(45) Date of Patent: Oct. 2, 2018

(54) METHOD AND SYSTEM FOR DETERMINING WHETHER A MONITORED INDIVIDUAL'S HAND(S) HAVE ENTERED A VIRTUAL SAFETY ZONE

(71) Applicant: CERNER INNOVATION, INC., Kansas City, KS (US)

(72) Inventors: Neil Kusens, Sherman Oaks, CA (US); Michael Kusens, Cooper City, FL (US)

(73) Assignee: Cerner Innovation, Inc., Kansas City, KS (US)

( * ) Notice: Subject to any disclaimer, the term of this patent is extended or adjusted under 35 U.S.C. 154(b) by 14 days.

(21) Appl. No.: 14/757,593

(22) Filed: Dec. 23, 2015

(65) Prior Publication Data

US 2016/0180668 A1    Jun. 23, 2016

Related U.S. Application Data

(60) Provisional application No. 62/096,289, filed on Dec. 23, 2014.

(51) Int. Cl.
*H04N 7/18* (2006.01)
*H04N 7/00* (2011.01)
*G16H 40/20* (2018.01)

(52) U.S. Cl.
CPC .................. *G16H 40/20* (2018.01)

(58) Field of Classification Search
CPC ... H04N 7/18; H04N 7/00; H04N 9/11; H04N 9/10; H04N 13/02; H04N 13/04
USPC ............ 348/154, 155, 156, 152, 61
See application file for complete search history.

(56) References Cited

U.S. PATENT DOCUMENTS

| | | |
|---|---|---|
| 4,669,263 A | 6/1987 | Sugiyama |
| 4,857,716 A | 8/1989 | Gombrich et al. |
| 5,031,228 A | 7/1991 | Lu |
| 5,276,432 A | 1/1994 | Travis |
| 5,448,221 A | 9/1995 | Weller |
| 5,482,050 A | 1/1996 | Smokoff et al. |
| 5,798,798 A | 8/1998 | Rector et al. |

(Continued)

FOREIGN PATENT DOCUMENTS

| | | |
|---|---|---|
| DE | 19844918 A1 | 4/2000 |
| WO | 2009018422 A1 | 2/2009 |
| WO | 2012122002 A1 | 9/2012 |

OTHER PUBLICATIONS

Pending U.S. Application by same inventor Neil Kusens, U.S. Appl. No. 14/575,850, filed Dec. 18, 2014, entitled "Method and Process for Determining Whether an Individual Suffers a Fall Requiring Assistance".

(Continued)

*Primary Examiner* — Daquan Zhao
(74) *Attorney, Agent, or Firm* — Shook, Hardy & Bacon L.L.P.

(57) ABSTRACT

A system and method that allows caregivers, central monitoring services, and other persons to monitor whether a monitored individual's hand(s) have entered into an area where the caregiver has determined the monitored individual's hand(s) should not be, such as where the monitored individual may remove or disturb a piece of medical equipment. Where the monitored individual's hand(s) do enter the restricted area that is represented by an electronic virtual safety zone, an alert can be generated by the system and method.

19 Claims, 14 Drawing Sheets

(56) References Cited

U.S. PATENT DOCUMENTS

| | | |
|---|---|---|
| 5,838,223 A | 11/1998 | Gallant et al. |
| 5,915,379 A | 6/1999 | Wallace et al. |
| 5,942,986 A | 8/1999 | Shabot et al. |
| 6,050,940 A | 4/2000 | Braun et al. |
| 6,095,984 A | 8/2000 | Amano et al. |
| 6,160,478 A | 12/2000 | Jacobsen et al. |
| 6,174,283 B1 | 1/2001 | Nevo et al. |
| 6,188,407 B1 | 2/2001 | Smith et al. |
| 6,269,812 B1 | 8/2001 | Wallace et al. |
| 6,287,452 B1 | 9/2001 | Allen et al. |
| 6,322,502 B1 | 11/2001 | Schoenberg et al. |
| 6,369,838 B1 | 4/2002 | Wallace et al. |
| 6,429,869 B1 | 8/2002 | Kamakura et al. |
| 6,614,349 B1 | 9/2003 | Proctor et al. |
| 6,727,818 B1 | 4/2004 | Wildman et al. |
| 6,804,656 B1 | 10/2004 | Rosenfeld et al. |
| 7,015,816 B2 | 3/2006 | Wildman et al. |
| 7,122,005 B2 | 10/2006 | Shusterman |
| 7,154,397 B2 | 12/2006 | Zerhusen et al. |
| 7,237,287 B2 | 7/2007 | Weismiller et al. |
| 7,323,991 B1 | 1/2008 | Eckert et al. |
| 7,408,470 B2 | 8/2008 | Wildman et al. |
| 7,420,472 B2 * | 9/2008 | Tran .................. A61B 5/103 340/539.1 |
| 7,430,608 B2 | 9/2008 | Noonan et al. |
| 7,502,498 B2 | 3/2009 | Wen et al. |
| 7,612,679 B1 | 11/2009 | Fackler et al. |
| 7,669,263 B2 | 3/2010 | Menkedick et al. |
| 7,715,387 B2 | 5/2010 | Schuman |
| 7,724,147 B2 | 5/2010 | Brown |
| 7,756,723 B2 | 7/2010 | Rosow et al. |
| 7,890,349 B2 | 2/2011 | Cole et al. |
| 7,895,055 B2 | 2/2011 | Schneider et al. |
| 7,908,153 B2 | 3/2011 | Scherpbier et al. |
| 7,945,457 B2 | 5/2011 | Zaleski |
| 7,962,544 B2 | 6/2011 | Torok et al. |
| 7,972,140 B2 | 7/2011 | Renaud |
| 8,108,036 B2 | 1/2012 | Tran |
| 8,123,685 B2 | 2/2012 | Brauers et al. |
| 8,224,108 B2 | 7/2012 | Steinberg et al. |
| 8,237,558 B2 | 8/2012 | Seyed Momen et al. |
| 8,273,018 B1 | 9/2012 | Fackler et al. |
| 8,432,263 B2 | 4/2013 | Kunz |
| 8,451,314 B1 | 5/2013 | Cline et al. |
| 8,529,448 B2 | 9/2013 | McNair |
| 8,565,500 B2 | 10/2013 | Neff |
| 8,620,682 B2 | 12/2013 | Bechtel et al. |
| 8,655,680 B2 | 2/2014 | Bechtel et al. |
| 8,700,423 B2 | 4/2014 | Eaton, Jr. et al. |
| 8,727,981 B2 | 5/2014 | Bechtel et al. |
| 8,769,153 B2 | 7/2014 | Dziubinski |
| 8,890,937 B2 | 11/2014 | Skubic et al. |
| 8,902,068 B2 | 12/2014 | Bechtel et al. |
| 8,917,186 B1 | 12/2014 | Grant |
| 8,953,886 B2 | 2/2015 | King et al. |
| 9,072,929 B1 | 7/2015 | Rush et al. |
| 9,129,506 B1 | 9/2015 | Kusens |
| 9,147,334 B2 | 9/2015 | Long et al. |
| 9,159,215 B1 * | 10/2015 | Kusens .................. G08B 21/22 |
| 9,269,012 B2 | 2/2016 | Fotland |
| 9,292,089 B1 | 3/2016 | Sadek |
| 9,305,191 B2 | 4/2016 | Long et al. |
| 9,408,561 B2 | 8/2016 | Stone et al. |
| 9,489,820 B1 | 11/2016 | Kusens |
| 9,519,969 B1 | 12/2016 | Kusens |
| 9,524,443 B1 | 12/2016 | Kusens |
| 9,536,310 B1 | 1/2017 | Kusens |
| 9,538,158 B1 | 1/2017 | Rush et al. |
| 9,563,955 B1 | 2/2017 | Kamarshi et al. |
| 9,597,016 B2 | 3/2017 | Stone et al. |
| 9,729,833 B1 | 8/2017 | Kusens |
| 9,741,227 B1 | 8/2017 | Kusens |
| 9,892,310 B2 | 2/2018 | Kusens et al. |
| 9,892,311 B2 | 2/2018 | Kusens et al. |
| 9,892,611 B1 | 2/2018 | Kusens |
| 9,905,113 B2 | 2/2018 | Kusens |
| 2002/0015034 A1 | 2/2002 | Malmborg |
| 2002/0077863 A1 | 6/2002 | Rutledge et al. |
| 2002/0101349 A1 | 8/2002 | Rojas, Jr. |
| 2002/0115905 A1 | 8/2002 | August |
| 2002/0183976 A1 | 12/2002 | Pearce |
| 2003/0037786 A1 | 2/2003 | Biondi et al. |
| 2003/0070177 A1 | 4/2003 | Kondo et al. |
| 2003/0092974 A1 | 5/2003 | Santoso et al. |
| 2003/0095147 A1 | 5/2003 | Daw |
| 2003/0135390 A1 | 7/2003 | O'Brien et al. |
| 2003/0140928 A1 | 7/2003 | Bui et al. |
| 2003/0227386 A1 | 12/2003 | Pulkkinen et al. |
| 2004/0019900 A1 | 1/2004 | Knightbridge et al. |
| 2004/0052418 A1 | 3/2004 | DeLean |
| 2004/0054760 A1 | 3/2004 | Ewing et al. |
| 2004/0097227 A1 | 5/2004 | Siegel |
| 2004/0116804 A1 | 6/2004 | Mostafavi |
| 2004/0193449 A1 | 9/2004 | Wildman et al. |
| 2005/0038326 A1 | 2/2005 | Mathur |
| 2005/0182305 A1 | 8/2005 | Hendrich |
| 2005/0231341 A1 | 10/2005 | Shimizu |
| 2005/0249139 A1 | 11/2005 | Nesbit |
| 2006/0004606 A1 | 1/2006 | Wendl |
| 2006/0047538 A1 | 3/2006 | Condurso et al. |
| 2006/0049936 A1 | 3/2006 | Collins et al. |
| 2006/0058587 A1 | 3/2006 | Heimbrock et al. |
| 2006/0089541 A1 | 4/2006 | Braun et al. |
| 2006/0092043 A1 | 5/2006 | Lagassey |
| 2006/0107295 A1 | 5/2006 | Margis et al. |
| 2006/0145874 A1 | 7/2006 | Fredriksson et al. |
| 2006/0261974 A1 | 11/2006 | Albert et al. |
| 2007/0085690 A1 | 4/2007 | Tran |
| 2007/0118054 A1 | 5/2007 | Pinhas et al. |
| 2007/0120689 A1 | 5/2007 | Zerhusen et al. |
| 2007/0129983 A1 | 6/2007 | Scherpbier et al. |
| 2007/0136218 A1 | 6/2007 | Bauer et al. |
| 2007/0159332 A1 | 7/2007 | Koblasz |
| 2007/0279219 A1 | 12/2007 | Warriner |
| 2007/0296600 A1 | 12/2007 | Dixon et al. |
| 2008/0001763 A1 | 1/2008 | Raja et al. |
| 2008/0002860 A1 | 1/2008 | Super et al. |
| 2008/0004904 A1 | 1/2008 | Tran |
| 2008/0009686 A1 | 1/2008 | Hendrich |
| 2008/0015903 A1 | 1/2008 | Rodgers |
| 2008/0071210 A1 | 3/2008 | Moubayed et al. |
| 2008/0087719 A1 | 4/2008 | Sahud |
| 2008/0106374 A1 | 5/2008 | Sharbaugh |
| 2008/0126132 A1 | 5/2008 | Warner et al. |
| 2008/0228045 A1 | 9/2008 | Gao et al. |
| 2008/0249376 A1 | 10/2008 | Zaleski |
| 2008/0267447 A1 | 10/2008 | Kelusky et al. |
| 2008/0277486 A1 | 11/2008 | Seem et al. |
| 2008/0281638 A1 | 11/2008 | Weatherly et al. |
| 2009/0082829 A1 | 3/2009 | Panken et al. |
| 2009/0091458 A1 | 4/2009 | Deutsch |
| 2009/0099480 A1 | 4/2009 | Salgo et al. |
| 2009/0112630 A1 | 4/2009 | Collins, Jr. et al. |
| 2009/0119843 A1 | 5/2009 | Rodgers et al. |
| 2009/0177327 A1 | 7/2009 | Turner |
| 2009/0224924 A1 | 9/2009 | Thorp |
| 2009/0278934 A1 * | 11/2009 | Ecker .................. G06K 9/00348 348/152 |
| 2009/0322513 A1 | 12/2009 | Hwang et al. |
| 2010/0117836 A1 | 5/2010 | Seyed Momen et al. |
| 2010/0169114 A1 | 7/2010 | Henderson et al. |
| 2010/0169120 A1 | 7/2010 | Herbst et al. |
| 2010/0172567 A1 | 7/2010 | Prokoski |
| 2010/0176952 A1 | 7/2010 | Bajcsy et al. |
| 2010/0188228 A1 | 7/2010 | Hyland |
| 2010/0205771 A1 | 8/2010 | Pietryga et al. |
| 2010/0245577 A1 | 9/2010 | Yamamoto et al. |
| 2010/0285771 A1 | 11/2010 | Peabody |
| 2010/0305466 A1 | 12/2010 | Corn |
| 2011/0018709 A1 | 1/2011 | Kornbluh |
| 2011/0022981 A1 | 1/2011 | Mahajan et al. |
| 2011/0025493 A1 | 2/2011 | Papadopoulos et al. |
| 2011/0025499 A1 | 2/2011 | Hoy et al. |
| 2011/0035057 A1 | 2/2011 | Receveur et al. |

(56) References Cited

U.S. PATENT DOCUMENTS

| | | | |
|---|---|---|---|
| 2011/0035466 A1 | 2/2011 | Panigrahi |
| 2011/0054936 A1 | 3/2011 | Cowan et al. |
| 2011/0068930 A1 | 3/2011 | Wildman et al. |
| 2011/0077965 A1 | 3/2011 | Nolte et al. |
| 2011/0087079 A1 | 4/2011 | Aarts |
| 2011/0102133 A1 | 5/2011 | Shaffer |
| 2011/0102181 A1 | 5/2011 | Metz et al. |
| 2011/0106560 A1 | 5/2011 | Eaton, Jr. et al. |
| 2011/0106561 A1 | 5/2011 | Eaton, Jr. et al. |
| 2011/0175809 A1 | 7/2011 | Markovic et al. |
| 2011/0190593 A1 | 8/2011 | McNair |
| 2011/0227740 A1 | 9/2011 | Wohltjen |
| 2011/0254682 A1 | 10/2011 | Sigrist Christensen |
| 2011/0288811 A1 | 11/2011 | Greene |
| 2011/0295621 A1 | 12/2011 | Farooq et al. |
| 2011/0301440 A1 | 12/2011 | Riley et al. |
| 2011/0313325 A1 | 12/2011 | Cuddihy |
| 2012/0025991 A1 | 2/2012 | O'Keefe et al. |
| 2012/0026308 A1 | 2/2012 | Johnson et al. |
| 2012/0075464 A1 | 3/2012 | Derenne et al. |
| 2012/0092162 A1 | 4/2012 | Rosenberg |
| 2012/0098918 A1 | 4/2012 | Murphy |
| 2012/0154582 A1 | 6/2012 | Johnson et al. |
| 2012/0212582 A1 | 8/2012 | Deutsch |
| 2012/0259650 A1 | 10/2012 | Mallon et al. |
| 2013/0027199 A1 | 1/2013 | Bonner |
| 2013/0120120 A1 | 5/2013 | Long et al. |
| 2013/0122807 A1 | 5/2013 | Tenarvitz et al. |
| 2013/0184592 A1 | 7/2013 | Venetianer |
| 2013/0309128 A1 | 11/2013 | Voegeli et al. |
| 2013/0332184 A1 | 12/2013 | Burnham et al. |
| 2014/0039351 A1 | 2/2014 | Mix et al. |
| 2014/0070950 A1 | 3/2014 | Snodgrass |
| 2014/0085501 A1 | 3/2014 | Tran |
| 2014/0155755 A1 | 6/2014 | Pinter et al. |
| 2014/0191861 A1 | 7/2014 | Scherrer |
| 2014/0267625 A1 | 9/2014 | Clark et al. |
| 2014/0327545 A1 | 11/2014 | Bolling et al. |
| 2014/0333744 A1 | 11/2014 | Baym et al. |
| 2014/0354436 A1 | 12/2014 | Nix et al. |
| 2014/0365242 A1 | 12/2014 | Neff |
| 2015/0109442 A1 | 4/2015 | Derenne et al. |
| 2015/0206415 A1 | 7/2015 | Wegelin et al. |
| 2015/0269318 A1 | 9/2015 | Neff |
| 2015/0278456 A1 | 10/2015 | Bermudez Rodriguez et al. |
| 2016/0022218 A1 | 1/2016 | Hayes et al. |
| 2016/0070869 A1 | 3/2016 | Portnoy |
| 2016/0093195 A1 | 3/2016 | Ophardt |
| 2016/0127641 A1 | 5/2016 | Gove |
| 2016/0253802 A1 | 9/2016 | Venetianer et al. |
| 2016/0267327 A1 | 9/2016 | Franz et al. |
| 2017/0055917 A1 | 3/2017 | Stone et al. |
| 2017/0109991 A1 | 4/2017 | Kusens |
| 2017/0143240 A1 | 5/2017 | Stone et al. |

OTHER PUBLICATIONS

Pending U.S. Application by same inventor Neil Kusens, U.S. Appl. No. 14/599,498, filed Jan. 17, 2015, entitled "Method and System for Determining Whether an Individual Takes Appropriate Measures to Prevent the Spread of Healthcare Associated Infections".

Pending U.S. Application by same inventor Neil Kusens, U.S. Appl. No. 14/611,363, filed Feb. 2, 2015, entitled "Method and System for Determining Whether an Individual Takes Appropriate Measures to Prevent the Spread of Healthcare Associated Infections ".

Pending U.S. Application by same inventor Neil Kusens, U.S. Appl. No. 14/623,349, filed Feb. 16, 2015, entitled "Method for Determining Whether an Individual Enters a Prescribed Virtual Zone Using 3D Blob Detection".

Pending U.S. Application by same inventor Neil Kusens, U.S. Appl. No. 14/724,969, filed May 29, 2015, entitled "Method and Process for Determining Whether an Individual Suffers a Fall Requiring Assistance".

Pending U.S. Application by same inventor Neil Kusens, U.S. Appl. No. 13/543,816, filed Jul. 7, 2012, entitled "Method and Process for Determining Whether an Individual Suffers a Fall Requiring Assistance".

Pending U.S. Application by same inventor Neil Kusens, U.S. Appl. No. 14/727,434, filed Jun. 1, 2015, entitled "Method for Determining Whether Enters a Prescribed Virtual Zone Using Skeletal Tracking and 3D Blob Detection".

Pending U.S. Application by same inventor Neil Kusens, U.S. Appl. No. 14/728,762, filed Jun. 2, 2015, entitled "Method for Determining Whether an Individual Leaves a Prescribed Virtual Perimeter".

Pending U.S. Application by same inventor Neil Kusens, U.S. Appl. No. 14/743,264, filed Jun. 18, 2015, entitled "System for Determining Whether an Individual Enters a Prescribed Virtual Zone Using 3D Blob Detection".

Pending U.S. Application by same inventor Neil Kusens, U.S. Appl. No. 14/743,499, filed Jun. 18, 2015, entitled "System for Determining Whether an Individual Suffers a Fall Requiring Assistance".

Pending U.S. Application by same inventor Neil Kusens, U.S. Appl. No. 14/743,447, filed Jun. 18, 2015, entitled "System for Determining Whether an Individual Suffers a Fall Requiring Assistance".

Pending U.S. Application by same inventor Neal Kusens. U.S. Appl. No. 14/611,363, filed Feb. 2, 2015, entitled "Method and System for Determining Whether an Individual Takes Appropriate Measures to Prevent the Spread of Healthcare Associated Infections ".

Pending U.S. Application by same inventor Neal Kusens, U.S. Appl. No. 14/613,866, filed Feb. 4, 2015, entitled "Method and System for Determining Whether an Individual Takes Appropriate Measures to Prevent the Spread of Healthcare Associated Infections Along With Centralized Monitoring".

Non-Final Office Action dated May 23, 2016 in U.S. Appl. No. 14/743,499, 5 pages.

Notice of Allowance dated May 31, 2016 in U.S. Appl. No. 14/743,447, 8 pages.

Notice of Allowance dated Jun. 22, 2016 in U.S. Appl. No. 14/743,447, 4 pages.

Notice of Allowance dated Jun. 27, 2016 in U.S. Appl. No. 14/728,762, 14 pages.

Non-Final Office Action dated Feb. 11, 2016 in U.S. Appl. No. 14/724,969, 14 pages.

Notice of Allowance dated Jul. 18, 2016 in U.S. Appl. No. 14/743,264, 16 pages.

Final Office Action dated Jul. 28, 2016 in U.S. Appl. No. 14/723,969, 26 pages.

Non-Final Office Action dated Mar. 11, 2016 in U.S. Appl. No. 14/575,850, 10 pages.

Tom Mooney, "Rhode Island ER first to test Google Glass on medical conditions", http://www.ems1.com/ems-products/cameras-video/articles/1860487-Rhode-Island-ER-first . . . printed on Mar. 11, 2014.

Notice of Allowance dated Dec. 23, 2016 in U.S. Appl. No. 14/724,969, 5 pages.

Non-Final Office Action dated Jan. 11, 2017 in U.S. Appl. No. 14/611,363, 19 pages.

Non-Final Office Action dated Feb. 23, 2017 in U.S. Appl. No. 14/757,877, 24 pages.

First Action Interview Preinterview Communication dated Feb. 24, 2017 in U.S. Appl. No. 15/395,716, 5 pages.

Notice of Allowance dated Mar. 20, 2017 in U.S. Appl. No. 14/613,866, 11 pages.

Non-Final Office Action dated Apr. 5, 2017 in U.S. Appl. No. 14/613,866, 15 pages.

Non-Final Office Action dated Oct. 7, 2015 in U.S. Appl. No. 14/339,397, 16 pages.

Notice of Allowance dated Aug. 26, 2016 in U.S. Appl. No. 14/743,447, 5 pages.

Notice of Allowance dated Sep. 19, 2016 in U.S. Appl. No. 14/743,499, 5 pages.

Notice of Allowance dated Oct. 14, 2016 in U.S. Appl. No. 14/743,264, 14 pages.

Notice of Allowance dated Nov. 9, 2016 in U.S. Appl. No. 14/743,264, 14 pages.

(56) References Cited

OTHER PUBLICATIONS

Notice of Allowance dated Nov. 14, 2016 in U.S. Appl. No. 14/743,447, 5 pages.
Non-Final Office Action dated Sep. 23, 2016 in U.S. Appl. No. 14/727,434, 9 pages.
Non-Final Office Action dated Apr. 11, 2017 in U.S. Appl. No. 15/285,416, 13 pages.
Notice of Allowance dated Apr. 19, 2017 in U.S. Appl. No. 15/395,716, 5 pages.
Notice of Allowance dated Apr. 21, 2017 in U.S. Appl. No. 14/724,969, 9 pages.
Notice of Allowance dated Apr. 25, 2017 in U.S. Appl. No. 14/727,434, 9 pages.
Non-Final Office Action dated May 31, 2017 in U.S. Appl. No. 14/599,498, 24 pages.
Final Office Action dated Apr. 28, 2017 in U.S. Appl. No. 14/611,363, 20 pages.
Non-Final Office Action dated Apr. 27, 2017 in U.S. Appl. No. 15/395,526, 16 pages.
Non-Final Office Action dated May 8, 2017 in U.S. Appl. No. 15/395,250, 19 pages.
Notice of Allowance dated Jul. 24, 2017 in U.S. Appl. No. 15/395,716, 5 pages.
Notice of Allowance dated Jul. 5, 2017 in U.S. Appl. No. 14/727,434, 9 pages.
Final Office Action dated Aug. 23, 2017 in U.S. Appl. No. 15/285,416, 16 pages.
Notice of Allowance dated Sep. 21, 2017 in U.S. Appl. No. 15/395,526, 13 pages.
Notice of Allowance dated Sep. 26, 2017 in U.S. Appl. No. 15/395,250, 13 pages.
Final Office Action dated Sep. 29, 2017 in U.S. Appl. No. 14/757,877, 22 pages.
Final Office Action dated Oct. 4, 2017 in U.S. Appl. No. 14/623,349, 30 pages.
Notice of Allowance dated Oct. 10, 2017 in U.S. Appl. No. 14/727,434, 9 pages.
Final Office Action dated Oct. 12, 2017 in U.S. Appl. No. 14/599,498, 28 pages.
Notice of Allowance dated Oct. 20, 2017 in U.S. Appl. No. 15/279,054, 14 pages.
Raheja, et al., "Human Facial Expression Detection From Detected in CapturedImage Using Back Propagation geural Network", International Journal of Computer Science and Information Technology (IJCSIT), vol. 2, No. 1, Feb. 2010, 8 pages.
Virtual Patient Observation: Centralize Monitoring of High-Risk Patients with Video-Cisco Video Surveillance Manager, https://www.cisco.com/c/en/us/products/collateral/physical-security/video-surveillance-manager/white paper_ C 11-715263.pdf.
First Action Interview Pre-Interview Communication dated Nov. 22, 2017 in U.S. Appl. No. 15/134,189, 4 pages.
Notice of Allowance dated Nov. 27, 2017 in U.S. Appl. No. 15/1279,054, 2 pages.
Notice of Allowance dated Dec. 6, 2017 in U.S. Appl. No. 15/395,716, 5 pages.
Final Office Action dated Dec. 12, 2017 in U.S. Appl. No. 14/575,850, 10 pages.
Notice of Allowance dated Dec. 29, 2017 in U.S. Appl. No. 14/611,363, 11 pages.
Notice of Allowance dated Jan. 18, 2018 in U.S. Appl. No. 15/279,054, 2 pages.
Non-Final Office Action dated Feb. 7, 2018 in U.S. Appl. No. 15/396,263, 19 pages.
Notice of Allowance dated Feb. 12, 2018 in U.S. Appl. No. 14/623,349, 12 pages.
Non-Final Office Action dated Feb. 22, 2018 in U.S. Appl. No. 14/599,498, 24 pages.
First Action Interview Office Action dated Feb. 22, 2018 in U.S. Appl. No. 15/134,189, 4 pages.
Non-Final Office Action dated Mar. 12, 2018 in U.S. Appl. No. 15/285,416, 20 pages.
Non-Final Office Action dated Mar. 14, 2018 in U.S. Appl. No. 14/757,877, 13 pages.
Non-Final Office Action dated May 2, 2018 in U.S. Appl. No. 15/728,110, 8 pages.
Non-Final Office Action dated May 7, 2018 in U.S. Appl. No. 14/611,363, 5 pages.
Non-Final Office Action dated May 8, 2018 in U.S. Appl. No. 15/148,151, 5 pages.
Notice of Allowance dated May 9, 2018 in U.S. Appl. No. 15/395,716, 5 pages.
First Action Interview Pre-Interview Communication dated May 21, 2018 in U.S. Appl. No. 15/910,645, 14 pages.
Non-Final Office Action dated May 31, 2018 in U.S. Appl. No. 15/395,762, 24 pages.
Non-Final Office Action dated May 31, 2018 in U.S. Appl. No. 15/848,621, 23 pages.
Non-Final Office Action dated Jun. 8, 2018 in U.S. Appl. No. 15/628,318, 9 new pages.
Notice of Allowance dated Jun. 13, 2018 in U.S. Appl. No. 14/575,850, 5 pages.
Notice of Allowance dated Jun. 18, 2018 in U.S. Appl. No. 14/623,349, 11 pages.
Notice of Allowance dated Jun. 19, 2018 in U.S. Appl. No. 15/395,716, 2 pages.
Final Office Action dated Jul. 12, 2018 in U.S. Appl. No. 15/134,189, 23 pages.
Final Office Action dated Jul. 5, 2018 in U.S. Appl. No. 15/285,416, 8 pages.
Non-Final Office Action dated Aug. 15, 2018 in U.S. Appl. No. 15/910,632, 7 pages.
Notice of Allowance dated Jul. 13, 2018 in U.S. Appl. No. 15/396,263, 9 pages.
Notice of Allowance dated Jul. 18, 2018 in U.S. Appl. No. 14/599,498, 6 pages.
Notice of Allowance dated Jul. 23, 2018 in U.S. Appl. No. 15/728,110, 15 pages.

* cited by examiner

METHOD AND SYSTEM FOR DETERMINING WHETHER A MONITORED INDIVIDUAL'S HAND(S) HAVE ENTERED A VIRTUAL SAFETY ZONE

CROSS-REFERENCE TO RELATED APPLICATIONS

This application claims the benefit of U.S. Provisional Application 62/096,289, filed on Dec. 23, 2014, which is herein incorporated by reference in its entirety.

TECHNICAL FIELD

The present disclosure relates to methods and systems for determining whether a monitored individual's hand or hands have entered a virtual safety zone.

BACKGROUND

Traditionally, monitoring of hospital patients is a costly, time-consuming endeavor. Of great concern to caregivers is a patient touching, removing, or otherwise disturbing medical equipment. If a patient disturbs an IV tube, breathing tube, catheter, or other medical equipment, significant negative repercussions can follow. These include healthcare-associated infections (HAIs), which are infections acquired by patients during the course of receiving treatment for other health conditions. According to recent studies, one in every twenty hospitalized patients will acquire an infection during the course of receiving healthcare treatment for a different condition, In terms of the economic impact, studies estimate the overall annual direct medical costs of HAIs range between $28.4 and $45 billion. The medical facility must typically bear the cost of the HAI, which puts a strain on the finances of the healthcare provider. In addition to HAIs, other serious injuries or even death can result from a patient's improper removal or disturbance of a piece of medical equipment.

BRIEF SUMMARY OF THE DISCLOSURE

This brief summary is provided as a general overview of the more detailed disclosure which follows. It is not intended to identify key or essential elements of the disclosure, or to define the claim terms in isolation from the remainder of the disclosure, including the drawings.

In general, this disclosure relates to systems, methods, and computer-readable storage media that notify caregivers or other monitors if a patient's hand(s) have entered into an area where the caregiver or monitor has determined that the patient's hand(s) should not be. For example, regardless of the patient's intent, it may be undesirable for patients to touch or manipulate certain medical equipment or temporary implants, such as nasogastric tubes, tracheal tubes, central lines, Intravenous (IV) lines, and the like. Simply touching the equipment may contaminate and/or disturb it. Further, disoriented and/or uncomfortable patients may attempt to reposition and/or remove medical equipment or temporary implants, which can cause injury—including possibly severe injury—to the patient. If the patient's activity involves the removal of sharp and/or body-fluid contaminated equipment, the patient's activity may also pose a risk to caregivers or others who approach the patient (e.g., because they could prick themselves and/or be exposed to blood- or other body fluid-borne pathogens). However, continuous visual monitoring of a patient is often impractical. Even in home care environments or other settings where the caregiver to patient ratio may be 1:1, there will be moments when a caregiver needs to tend tasks that may take them out of visual range of the patient.

In some aspects, a method is disclosed for detecting when a monitored individual has moved on or both of his or her hands within a virtual safety zone. The method may comprise configuring a virtual safety zone around an area where the individual to be monitored is located. The method may comprise providing one or more 3D motion sensors to capture live video data from the area. The method may comprise forwarding the video data from the one or more 3D motion sensors to a computerized monitoring system. The method may comprise determining, as by the computerized monitoring system, when the monitored individual has moved at least one of his or her hands within the virtual safety zone. The method may comprise electronically transmitting an alert to a centralized monitoring system, by the computerized monitoring system, when the computerized monitoring system determines that the monitored individual has moved at least one of his or her hands within the virtual safety zone.

The method may comprise determining whether the at least one hand of the monitored individual remained within the virtual safety zone for a predetermined period of time before electronically transmitting an alert to the centralized monitoring system. The method may comprise continuously displaying a live video feed of the monitored area received from the one or more 3D motion sensors on a centralized monitoring alert display after it has been determined that at least one hand of the monitored individual is within the virtual safety zone for the predetermined period of time. The method may comprise continuously displaying a live video feed of the monitored area received form the one or more 3D motion sensors on a centralized monitoring primary display that is remotely located from the monitored area. The method may comprise continuously displaying a live feed of the monitored area received form the one or more 3D motion sensors on a centralized monitoring alert display after it has been determined that at least one hand of the monitored individual is within the virtual safety zone, wherein the centralized monitoring alert display is a separate display from the centralized monitoring primary display.

The method may comprise continuously displaying a live video feed of the monitored area received from the one or more 3D motion sensors after it has been determined that at least one hand of the monitored individual is within the virtual safety zone. The method may comprise updating a database in communication with the computerized monitoring system regarding the determination that at least one hand of the monitored individual was within the virtual safety zone. The method may comprise notifying a designated caregiver by electronic message regarding the determination that at least one hand of the monitored individual was within the virtual safety zone. The virtual safety zone may encompass at least part of the monitored individual's face. Determining, by the computerized monitoring system, when the monitored individual has moved at least one of his or her hands within the virtual safety zone may comprise using facial tracking to monitor the virtual safety zone. Determining, by the computerized monitoring system, when the monitored individual has moved at least one of his or her hands within the virtual safety zone may comprise determining that the face of the monitored individual is at least partially obscured.

In some aspects, the disclosure relates to a system for determining whether a monitored individual has placed one or both hands in a virtual safety zone. The system may comprise one or more 3D motion sensors co-located with a monitored individual. The system may comprise a computerized monitoring system. The computerized monitoring system may be configured to receive data from the one or more 3D motion sensors. The computerized monitoring system may be configured to identify the position of the monitored individual's hands. The computerized monitoring system may be configured to determine whether at least one of the monitored individual's hands have entered a virtual safety zone. The system may comprise a computerized communication system. The computerized communication system may be configured to receive from the computerized monitoring system a determination that at least one of the monitored individual's hands have entered a virtual safety zone. The computerized communication system may be configured to send an alert of the entry into the virtual safety zone to at least one designated recipient.

The computerized monitoring system may be further configured to actuate a timer upon determining that the monitored individual's hand or hands have entered a virtual safety zone. The computerized monitoring system may send to the computerized communication system a determination that the monitored individual's hand or hands have entered a virtual safety zone only if the monitored individual's hand or hands remain in the virtual safety zone for at least a predetermined period of time. The designated recipient of the alert may include one or more of a caregiver, the monitored individual, an alternate caregiver, and a supervisor. The alert may comprise an audible instruction to the patient. The system may further comprise a database for logging events related to the entry of the monitored individual's hand or hands into the virtual safety zone. The computerized communication system may further be configured to save log entries for events related to the entry of the monitored individual's hand or hands into the virtual safety zone and related alerts.

In some aspects, the disclosure relates to computer-readable storage media having stored thereon executable instructions. When executed by a computer, the instructions may cause the computer to receive visual data from one or more 3D motion sensors. The instructions may cause the computer to identify a monitored individual's location from the visual and/or sound data. The instructions may cause the computer to establish a virtual safety zone at least partially overlapping the monitored individual's location. The instructions may cause the computer to identify the monitored individual's hands from the visual data. The instructions may cause the computer to determine whether one or both of the monitored individual's hands enter the virtual safety zone from the visual data. The instructions may cause the computer to time the duration for which the monitored individual's hand or hands remain in the virtual safety zone. The instructions may cause the computer to alarm if the monitored individual's hand or hands remain in the virtual safety zone for longer than a predetermined period. The instructions may cause the computer to present a human-readable visual image of the monitored individual's location to a display device. The instructions may cause the computer to accept user input to define the virtual safety zone. The instructions may cause the computer to log alerts in a database.

Additional objects, advantages, and novel features of the disclosure will be set forth in part in the description which follows, and in part will become apparent to those skilled in the art upon examination of the following, or may be learned by practice of the disclosure.

BRIEF DESCRIPTION OF THE SEVERAL VIEWS OF THE DRAWING

The present disclosure references the attached drawing figures, wherein.

DETAILED DESCRIPTION

As mentioned above, patients, particularly, but not exclusively, patients who are disoriented or uncomfortable, may resort to self-help and attempt to reposition or remove medical equipment and/or temporary implants. When nasogastric, tracheal, central, IV, or other lines or equipment are disturbed by the patient, they may become contaminated by the patient's hand and contribute to the development of infection. Further, if lines or equipment are removed improperly, the patient can injure himself or herself. This is sometimes described in terms of a patient, however, the term "monitored individual" is meant to encompass both "patients" in the sense of individuals under immediate medical care, such as patients in an in-patient setting, as well as individuals who may use certain medical equipment and/or temporary implants in other settings, including, without limitation, assisted living facilities, nursing homes, hospice care, home care, outpatient settings, and the like.

The monitoring may be done by a caregiver. A caregiver may be a medical professional or paraprofessional, such as an orderly, nurse's aide, nurse, or the like. A caregiver may also be a friend, relative, individual, company, or facility that provides assistance with daily living activities and/or medical care for individuals, such as individuals who are disabled, ill, injured, elderly, or otherwise in need of temporary or long-term assistance.

Figure 1:
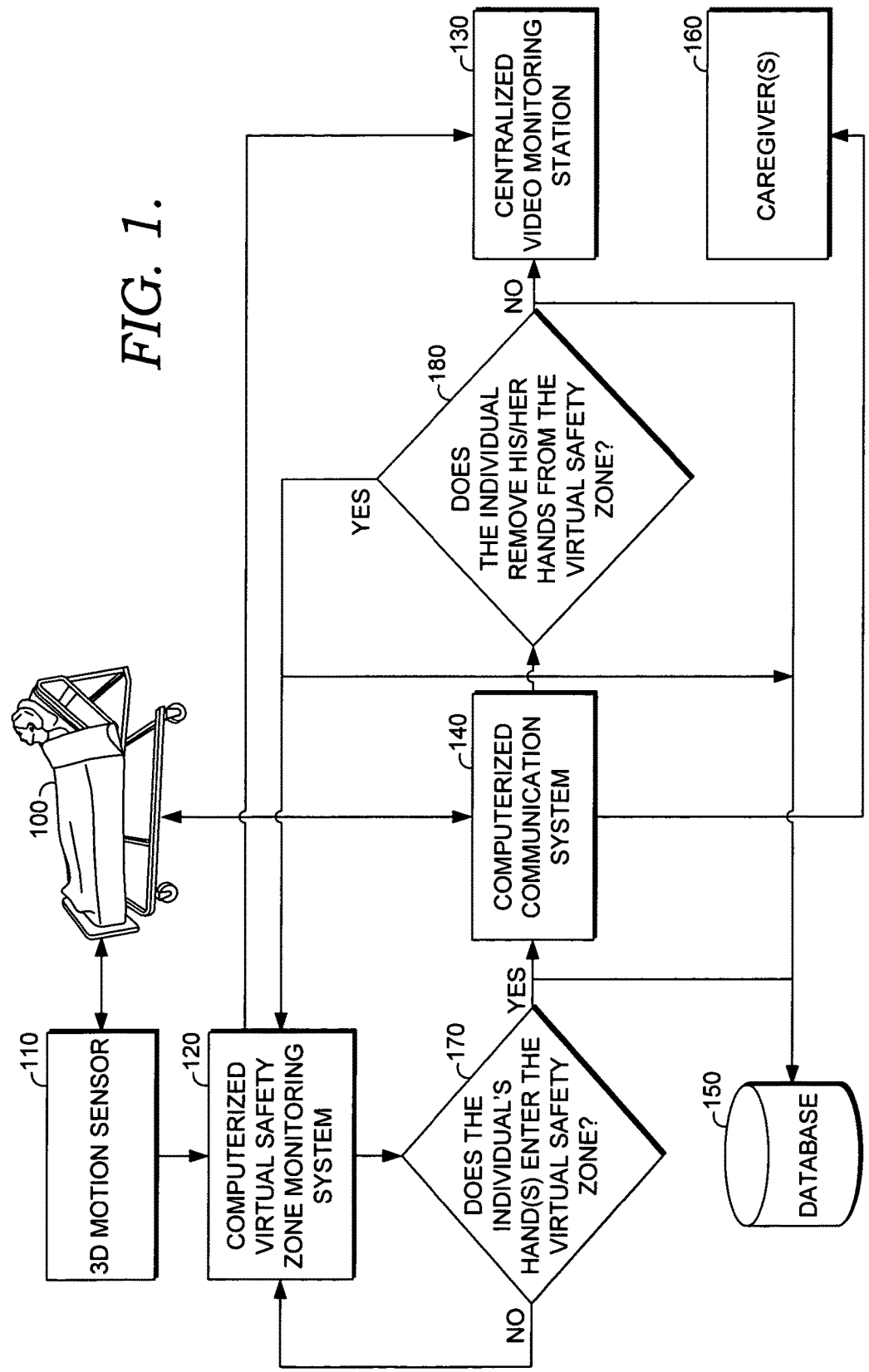
FIG. 1 is a flowchart for an exemplary method for determining whether a monitored individual's hands have entered a virtual safety zone.

FIG. 1 shows an exemplary workflow for monitoring whether a monitored individual's hand(s) have encroached into a predefined virtual safety zone through the use of 3D motion sensors. A 3D motion sensor is an electronic device that contains one or more cameras capable of identifying individual objects, people and motion regardless of lighting conditions. The 3D motion sensor may further contain one or more microphones to detect audio. The cameras can utilize technologies including but not limited to color RGB, CMOS sensors, lasers, infrared projectors and RF-modulated light. The 3D motion sensor may have one or more integrated microprocessors and/or image sensors to detect and process information both transmitted from and received by the various cameras. Exemplary 3D motion sensors include the Microsoft® Kinect® Camera, Sony® PlayStation® Camera, and the Intel® RealSense™ Camera, each of which happens to include microphones, although sound capture is not essential to the practice of the disclosure.

The microprocessor of the 3D motion sensor may be configured to calculate a change in location of the person or object of interest over a period of time, if a change has occurred. As a non-limiting example, a person's right hand can be at time $T_1$ located at coordinates $(x_1, y_1, z_1)$ in a picture frame taken by the camera. At time $T_2$ the right hand is captured by the picture frame taken by the camera at coordinates $(x_2, y_2, z_2)$. Based on this information, motion, speed and direction can be derived utilizing the elapsed time and comparing the two 3D coordinates over the elapsed time. As opposed to conventional motion sensors, which use captured motion to control a camera, the 3D motion and/or sound sensor described herein uses the camera in order to compute the motion.

The 3D motion and/or sound sensors may operate continuously, or intermittently (for example, running for a fixed period at defined intervals, such as periods when the monitored individual might be expected to be awake, or to be disoriented, or to otherwise merit monitoring), or on a trigger (e.g., when a motion detector or light sensor is activated, suggesting activity in the room). The camera/sensors are preferably continuously on at all times while the monitoring is occurring, regardless of whether the person or object of interest is moving or not. The camera preferably views the entire room or a large portion of the room simply by its placement in a manner sufficient for the room to be visible to the camera.

The 3D motion sensors may record video. Video is technically made up of individual picture frames (i.e. 30 frames per second of video).

One or more 3D motion sensors 110 may be located within the room of the patient or individual being monitored 100 and potentially just outside of the monitored individual's room, home, hospital room, or other place of temporary or permanent residence. Placing a 3D sensor just outside a monitored individual's room may help the system detect visitors, caregivers, or others who are not the monitored individual a few moments sooner than if there were sensors only inside the room. Detecting others earlier may help the system track the others and distinguish others from the monitored individual without an apparent delay in processing or displaying the sensor data, or with a reduced delay in processing or displaying the sensor data. The 3D motion sensor is connected to the computerized virtual safety zone monitoring system 120 via a data connection (USB, TCP/IP or comparable).

The one or more 3D motion sensors 110 can be configured to recognize the monitored individual 100 and other individuals using biometric identifiers such as facial tracking, height, distance between points on the body, etc. Alternately or additionally, the monitored individual 100 can be identified by means of a user creating a three-dimensional zone around the monitored individual 100 through the software application. Once a monitored individual 100 is identified, the software can automatically generate or allow the user to generate a configurable three-dimensional virtual safety zone 500 where the caregiver wants to prevent a monitored individual's hand(s) from entering.

Data from the one or more 3D motion sensors 110 are sent to a computerized virtual safety zone monitoring system 120. The computerized virtual safety zone monitoring system 120 (or "computerized monitoring system") is a computer programmed to monitor transmissions of data from the 3D motion sensor 110. The computerized monitoring system may be integral to the 3D motion sensor 110 or a distinctly separate apparatus from the 3D motion sensor 110, possibly in a remote location from 3D motion sensor 110 provided that the computerized monitoring system 120 can receive data from the 3D motion sensor 110. The computerized monitoring system 120 may be located in the monitored individual's room or location. The computerized monitoring system 120 may be connected to a centralized video monitoring station (or "centralized monitoring station") 130. The computerized monitoring system 120 and centralized monitoring station 130 may be remotely located at any physical locations so long as a data connection exists (TCP/IP or comparable) between the computerized monitoring system 120, the computerized communication system 140 (if separate from computerized monitoring system 120), the centralized monitoring station 130, and the 3D motion sensor(s) 110.

The computerized communication system 140 is a computer programmed to facilitate communication between the monitored individual 100 and computerized monitoring system 120 in the event the monitored individual 100 has placed one or both hands in a virtual safety zone. The computerized communication system 140 may include, but is not limited to, amplified speakers, microphones, lights, monitors, computer terminals, mobile phones and/or other technologies to allow for the electronic communication to take place. The computerized communication system may preferably be located within the monitored individual's room, however, certain components of the system are mobile by their nature (i.e. mobile phones, pagers, certain computers, such as laptop or tablet computers) and could be located at any location so long as a data connection (TCP/IP or comparable) exists between the computerized monitoring system 120, the computerized communication system 140, centralized monitoring station 130 and 3D motion sensor 110.

The computerized virtual safety zone monitoring system 120 provides the centralized monitoring station 130 with visual telemetry of the monitored individual 100. This information is received from one or more computerized monitoring systems 120, computerized communication systems 140 and/or 3D motion sensors 110. The centralized video monitoring system 130 displays the information in an organized manner to an individual or group of individuals assigned to monitor the monitored individuals. The centralized video monitoring system 130 may be located with or near the monitored individual, e.g., at a nursing station on the same floor as a hospital patient, or may be located remotely from the monitored individual. As one example, a computerized virtual safety zone monitoring system 120 used with a 3D motion sensor 110 in a home environment may be monitored by an agency or individual in a different part of a building, a different building, or even a different city. The computerized monitoring system 120 receives the raw data from the camera sensor, processes the raw data, e.g., to determine whether a monitored individual's hand or hands have entered a virtual safety zone, and transmits at least visual telemetry, possibly with sound telemetry, alert information, and/or other data, to the centralized monitoring station 130.

Figure 2:
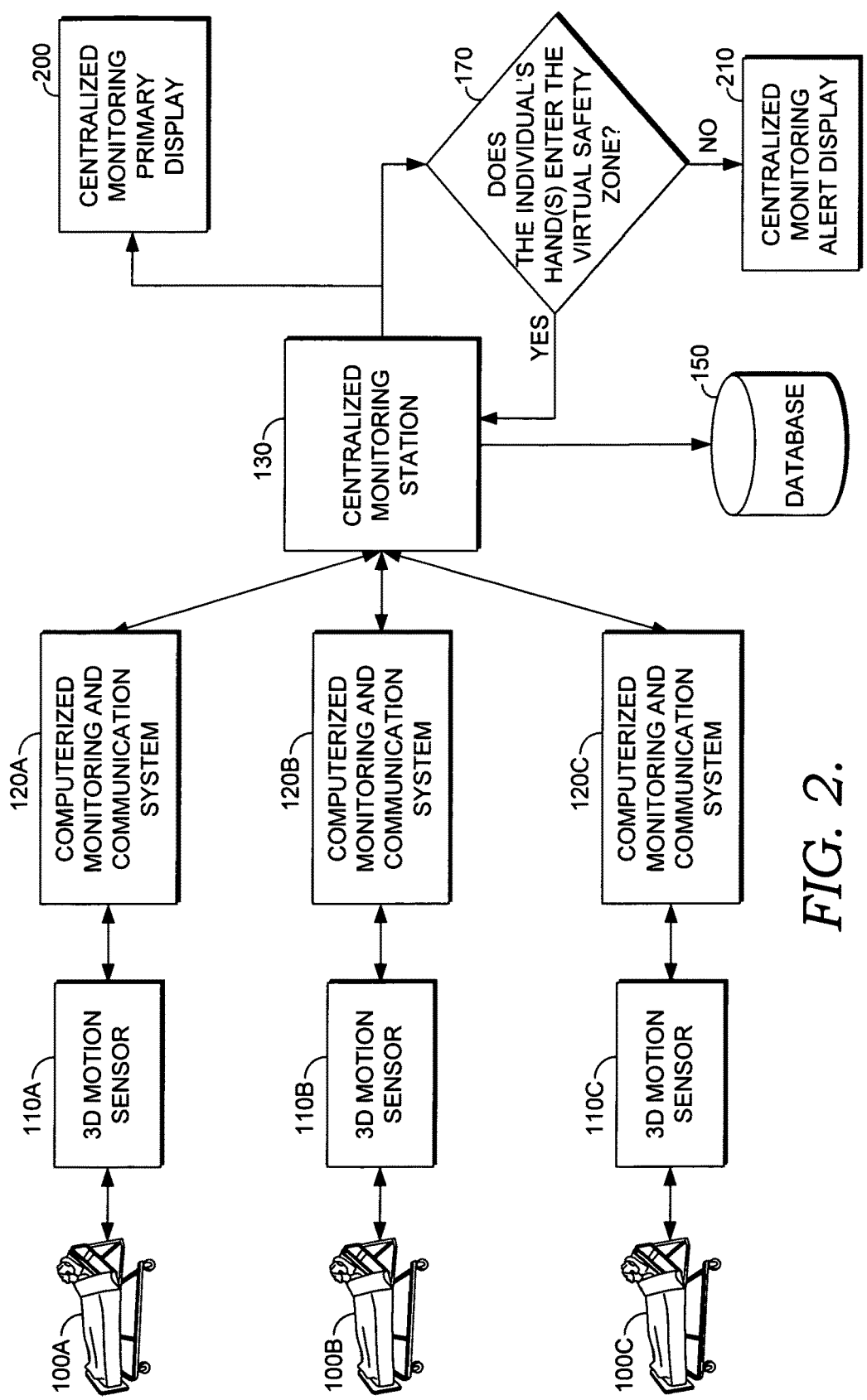
FIG. 2 is an exemplary system for centralized monitoring to determine whether a monitored individual's hands have entered a virtual safety zone.

The centralized monitoring station 130 may comprise a primary display 200, as shown in FIG. 2. The centralized monitoring station primary display 200 may be connected to the centralized monitoring station 130, and may show video and/or audio of all locations being monitored at the centralized monitoring station 130. If audio telemetry is available, it may be selectable for a particular location, so as to prevent overlapping audio feeds from becoming unintelligible. The centralized monitoring station 130 may comprise an alert display 210. The centralized monitoring alert display 210 may be a physically separate display from the centralized monitoring primary display 200, e.g., a separate video display screen or screens. Alternately, or additionally, centralized monitoring alert display 210 may be a portion of centralized monitoring primary display 200, or may be presented as a change in appearance, formatting, positioning, or the like in centralized monitoring primary display 200.

Figure 3:
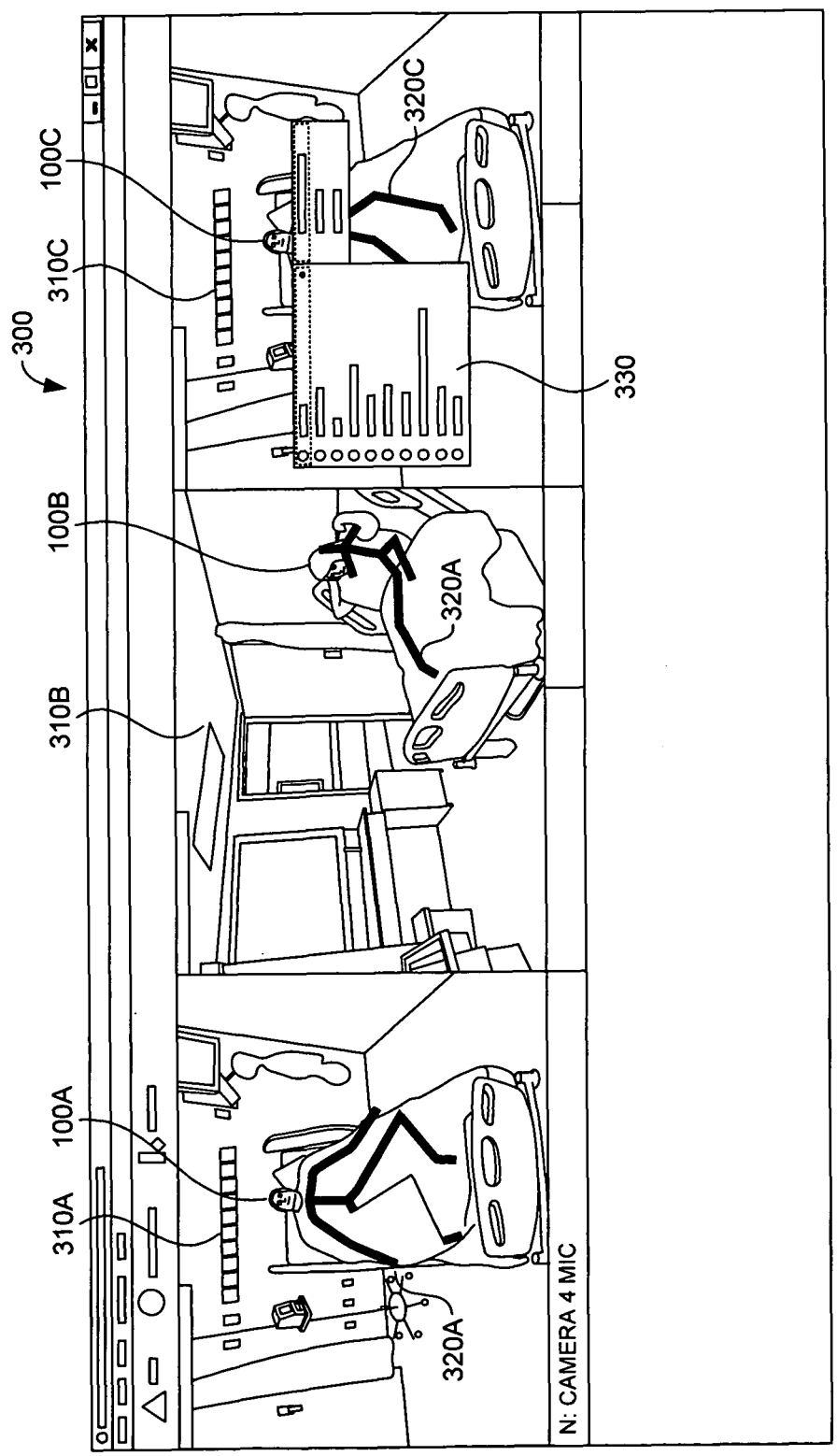
FIG. 3 is an exemplary rendering of a composite screen showing three monitored individuals.

FIG. 3 shows an exemplary display 300 of visual telemetry data for multiple monitored individuals 100A, 100B, and 100C, in simultaneous views 310A, 310B, and 310C, respectively, as might be configured on centralized monitoring station primary display 200. As shown, views 310A, 310B, and 310C appear on a split screen, however, different views could also be shown on separate displays. In addition to showing monitored individuals 100A, 100B, and 100C, display 300 shows skeleton figures 320A, 320B, and 320C for each monitored individual. In addition, view 310C shows a pop-up menu 330, which may present configuration options for view 310C or options for responding to an alarm associated with monitored individual 100C or both.

Figure 4:
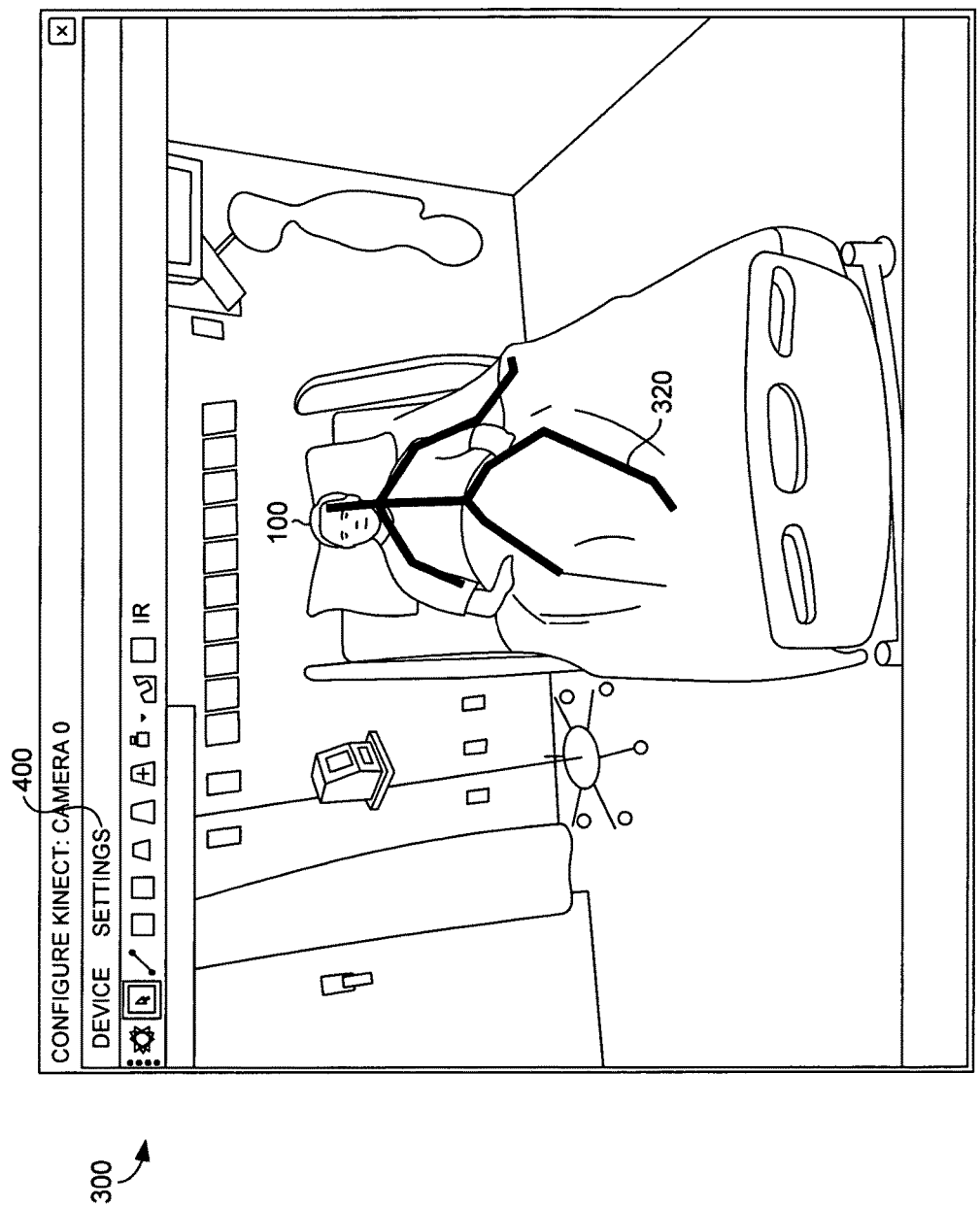
FIG. 4 is an exemplary view of the monitoring image of a monitored individual.
Figure 5:
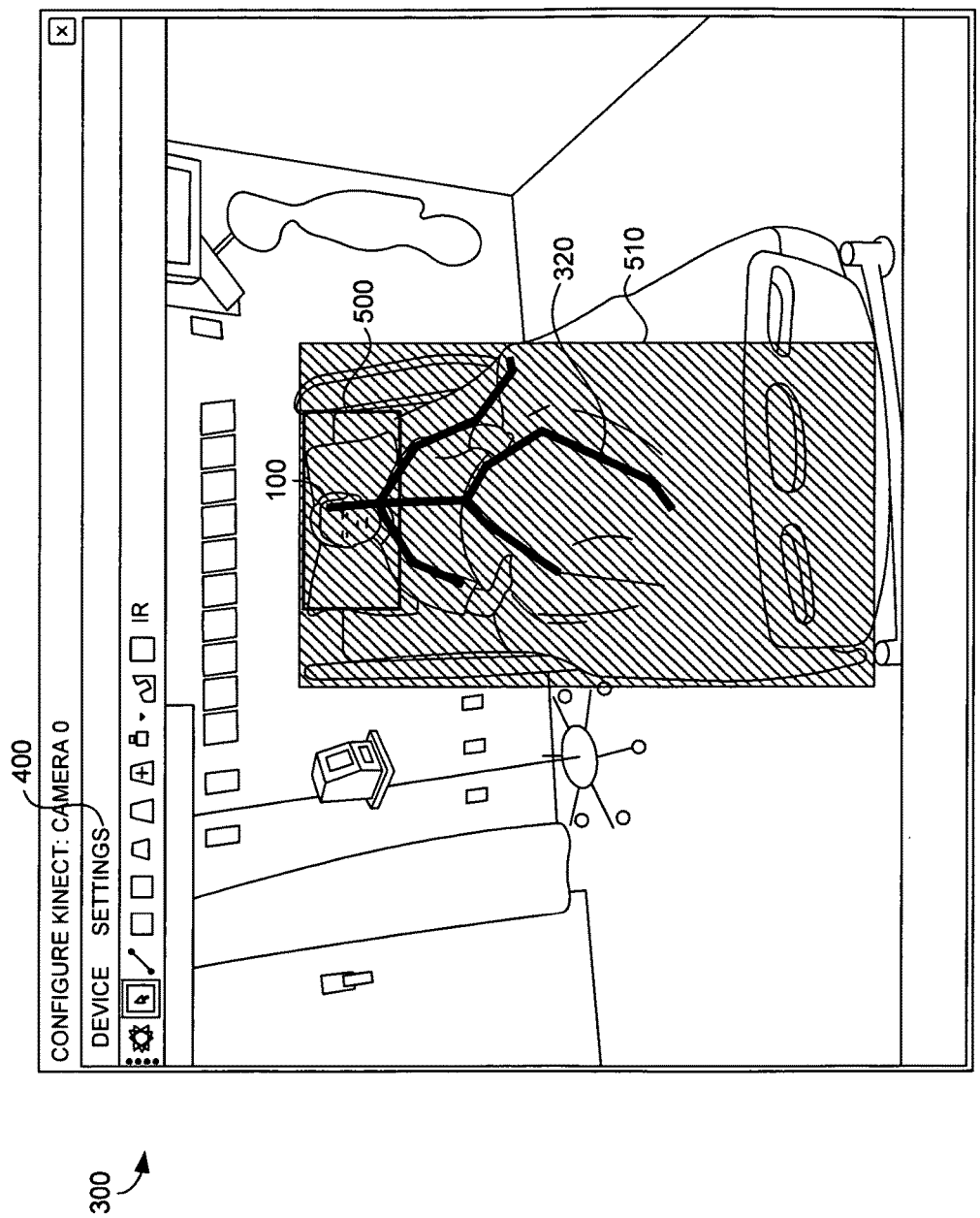
FIG. 5 is a rendering of an exemplary virtual safety zone.

FIG. 4 shows an exemplary display 300 of visual telemetry data for a single monitored individual 100, with skeleton figure 320 and menu 400. FIG. 5 shows the same exemplary display 300 as FIG. 4 after a user has selected a menu option to define and/or confirm a virtual safety zone 500 and a bed zone 510. The virtual safety zone 500 and/or bed zone 510 may be automatically generated by the computerized monitoring system 120. For example, computerized monitoring system 120 may define a virtual safety zone 500 around skeleton figure 320 by generating a perimeter using a default average distance from key skeleton points, such as face or shoulder landmarks to the perimeter. A bed zone 510 may be defined by computerized monitoring system 120, for example, by generating a perimeter using a default average distance from the perimeter of bed zone 510 to skeleton figure 320. While the virtual safety zone 500 defines an area where the caregiver does not want the monitored individual's hand(s), the bed zone 510 may be used to "lock on to" the monitored individual, so that the tracking algorithms do not inadvertently shift to caregivers or visitors if different individuals' body parts cross in the camera view during interactions between the monitored individual and others. Although described as a "bed" zone, bed zone 510 need not be centered on a bed. A bed zone 510 may be defined based on the monitored individual's skeleton figure, or may be defined around other furniture or medical equipment supporting the monitored individual, such as a chair, chaise longue, surgical table, etc.

The virtual safety zone 500 and/or bed zone 510 may be defined in 2 dimensions, e.g., as a perimeter around at least a portion of skeleton figure 320. Virtual safety zone 500 may encompass at least a portion of the monitored individual's head, neck, shoulders, and/or chest. Virtual safety zone 500 and bed zone 510 are depicted as rectangular, however, any desired shape could be used, including, without limitation, circles, squares, triangles, ovals, other regular shapes, or irregular shapes. By selecting a configuration option from menu 400, a user may alter or reset the perimeter that defines virtual safety zone 500.

Figure 6:
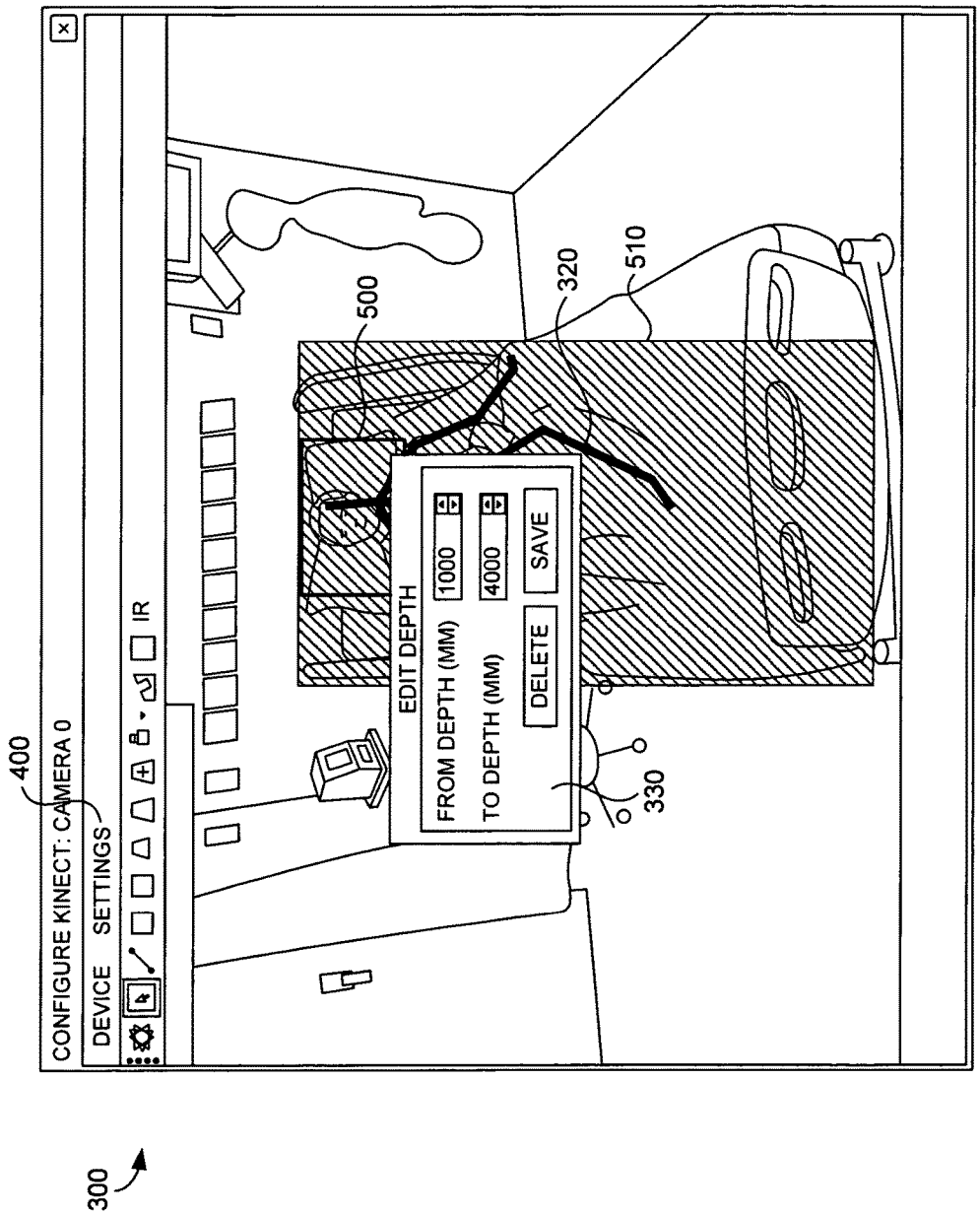
FIG. 6 is an exemplary interface for configuring a virtual safety zone.

As shown in FIG. 6, the virtual safety zone 500 may have a third dimension of depth, e.g., be defined as a volume around at least a portion of skeleton figure 320. As with the perimeter of virtual safety zone 500, the depth of virtual safety zone may be automatically generated by the computerized monitoring system 120. By selecting a configuration option from menu 400, a user may alter or reset the depth that defines virtual safety zone 500 using a pop-up menu 330. Alternately, the perimeter and/or depth of virtual safety zone 500 may be determined entirely by a system user, such as by entering coordinates or distances, as shown in pop-up menu 330 in FIG. 6, or by providing selection tools like drag-and-drop and pull-to-expand boxes or other shapes. Virtual safety zone 500 may be most often used around the head, neck, shoulders and/or chest. Virtual safety zone 500 could be used around other body parts, such as an arm or a leg, however, bedding, dining tables, and other objects may be more likely to obscure the view of other body parts and cause false alarms or missed alarms.

Figure 7:
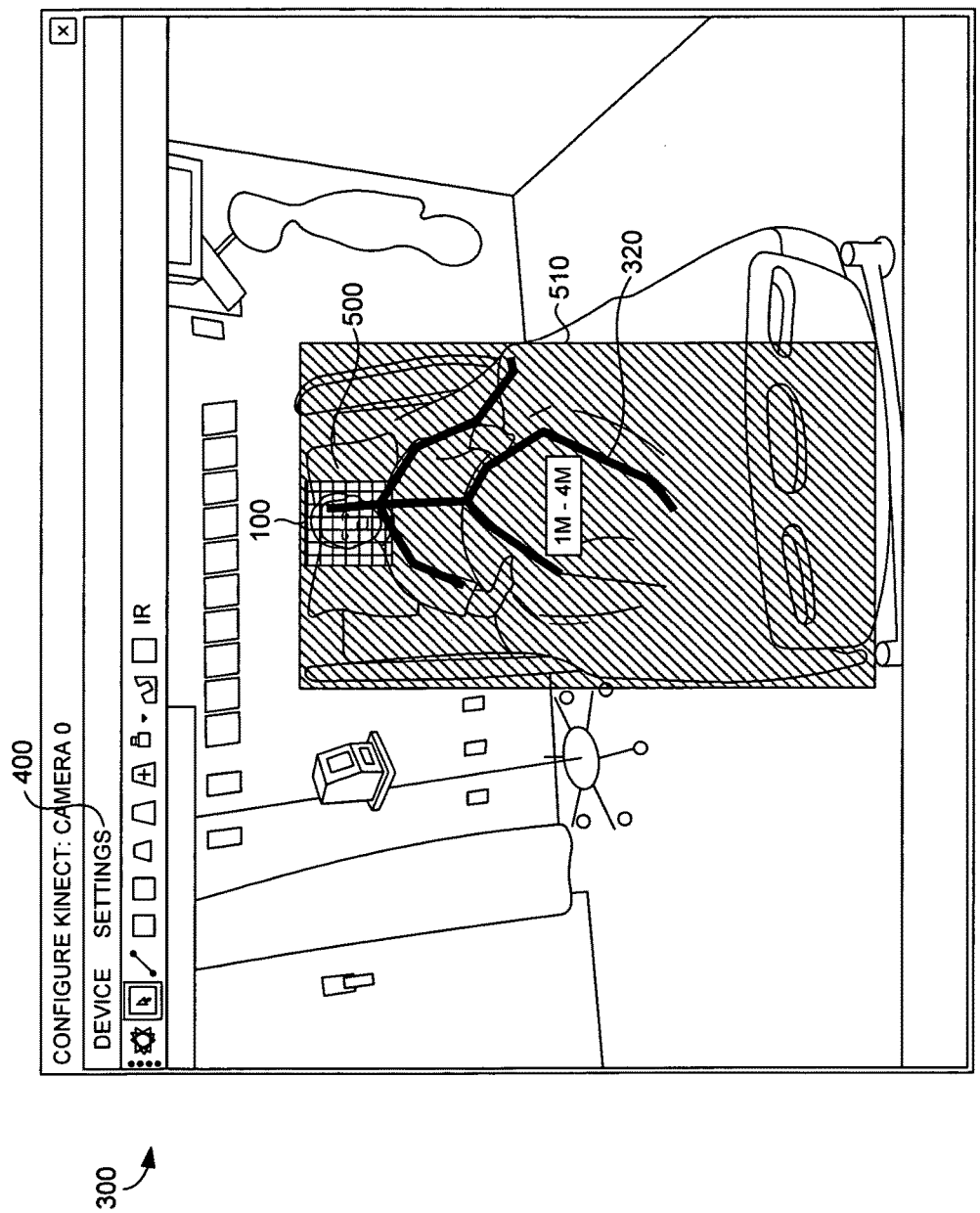
FIG. 7 is an exemplary display of a monitored individual overlaid with a virtual safety zone.
Figure 8:
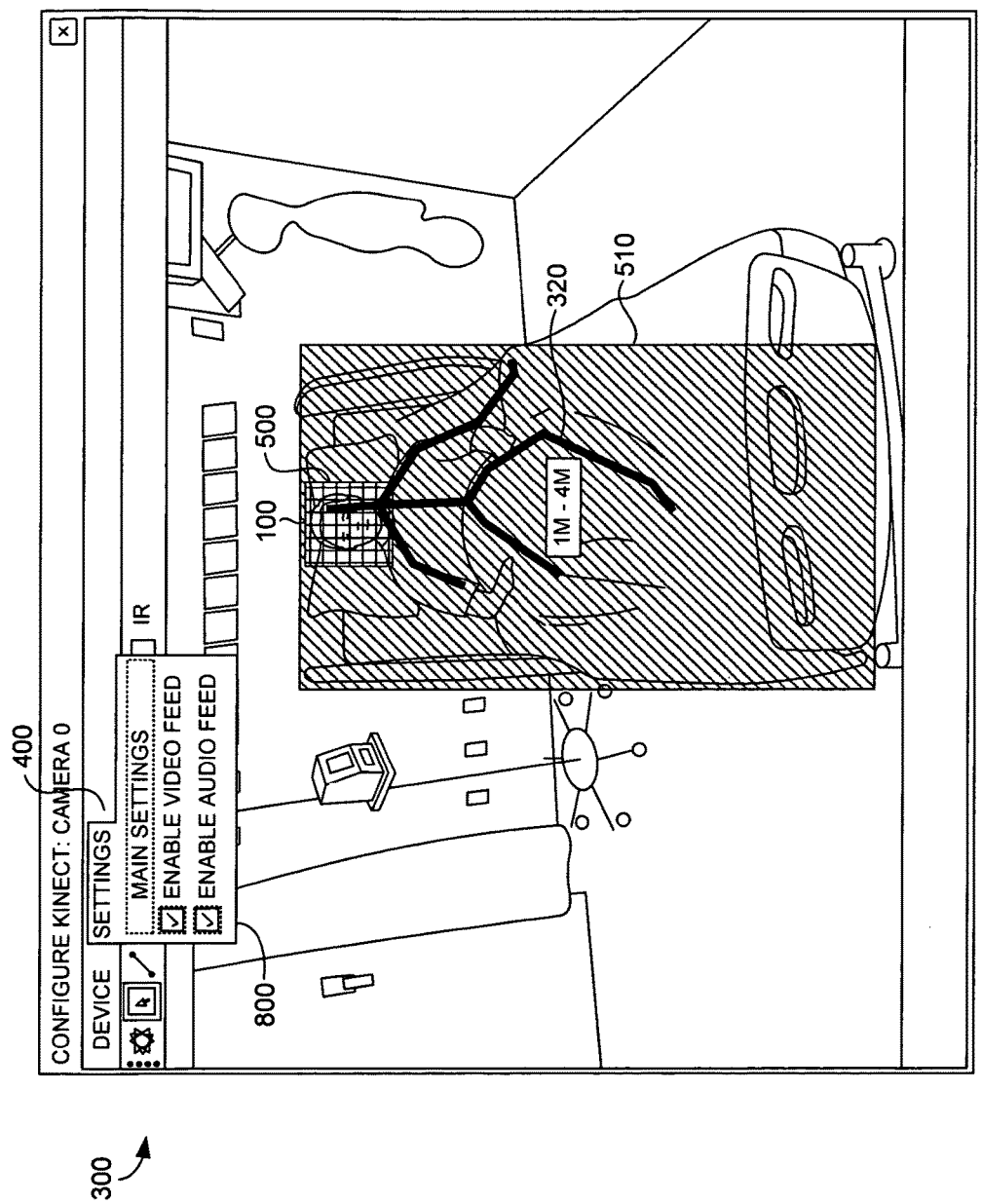
FIG. 8 is an exemplary interface for configuring options for monitoring an individual.

FIG. 7 shows a configured virtual safety zone 500 overlaid on visual telemetry for a monitored individual 100. FIG. 8 shows additional configuration options 800 from menu 400, allowing a user to select whether to display video telemetry ("VIDEO FEED"), audio telemetry ("AUDIO FEED"), or both.

Figure 9:
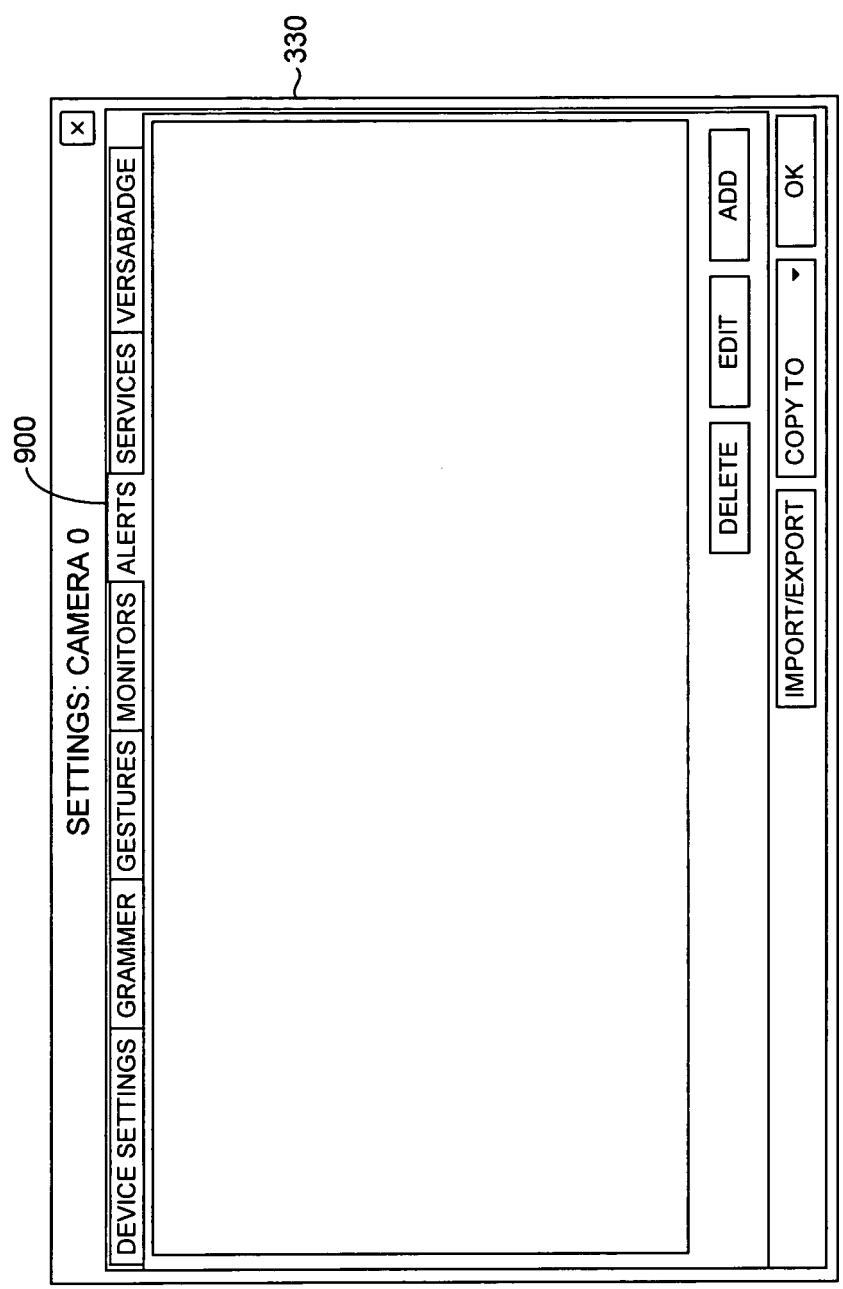
FIG. 9 is an exemplary interface for configuring a monitoring system.
Figure 10:
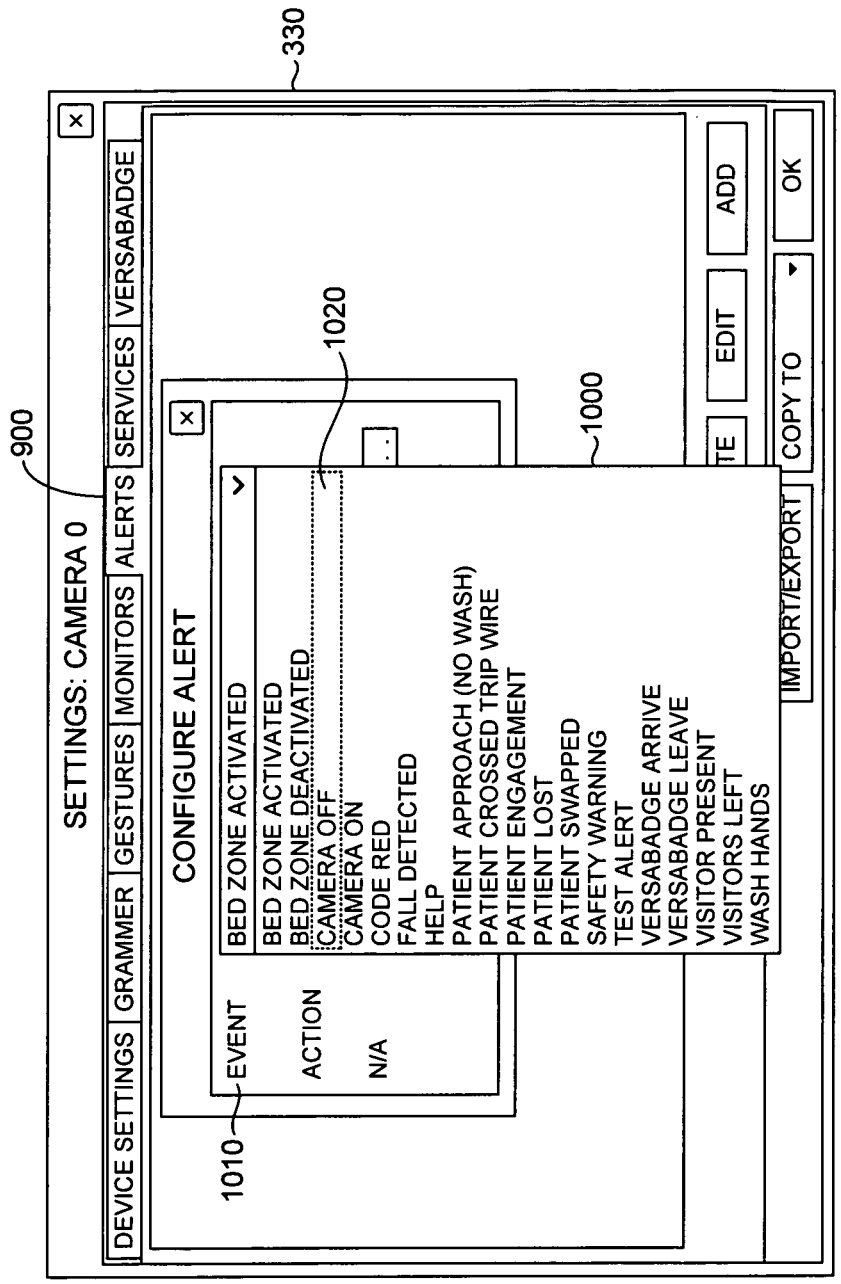
FIG. 10 is an exemplary interface for configuring a monitoring system.
Figure 11:
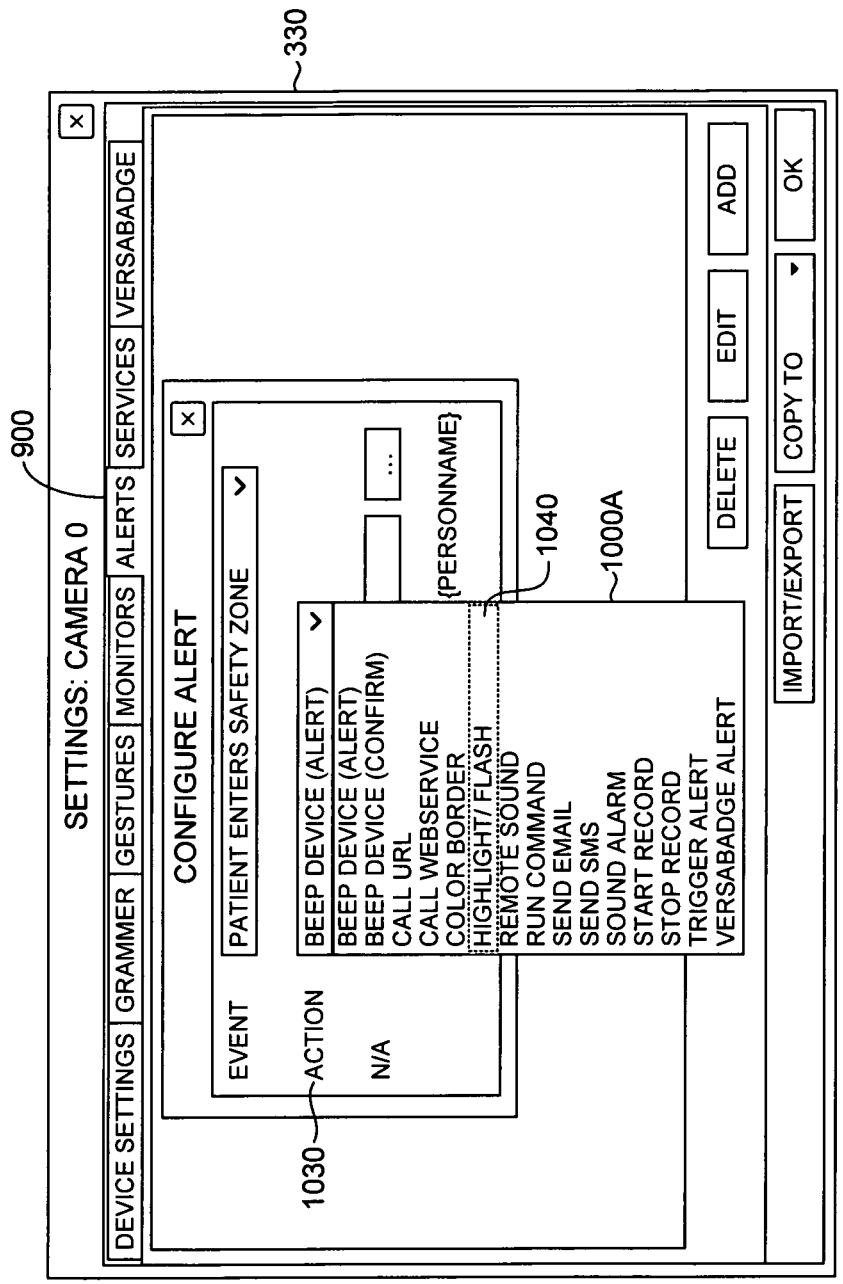
FIG. 11 is an exemplary interface for configuring a monitoring system.

FIG. 9 shows exemplary configuration settings in a pop-up menu 330. Tab 900 presents an exemplary tab for configuring alerts that might be issued if the monitored individual 100 places one or both hands inside virtual safety zone 500, or places one or both hands inside virtual safety zone 500 for longer than a predetermined period of time. FIG. 10 shows a drop down menu 1000 as may appear upon selection of alerts tab 900. A user may be asked to configure an alert for a particular kind of event 1010. As shown in FIG. 10, the user has elected to set an alert for when the camera (e.g., 3D motion sensor 110) is turned off. FIG. 11 shows the configuration of an action 1030 from dropdown menu 1000A. As shown in FIG. 11, the user has selected highlight/flash 1040, a setting that changes the appearance of the display border, text, or other properties on centralized monitoring primary display 200, centralized monitoring alert display 210, or both.

Figure 12:
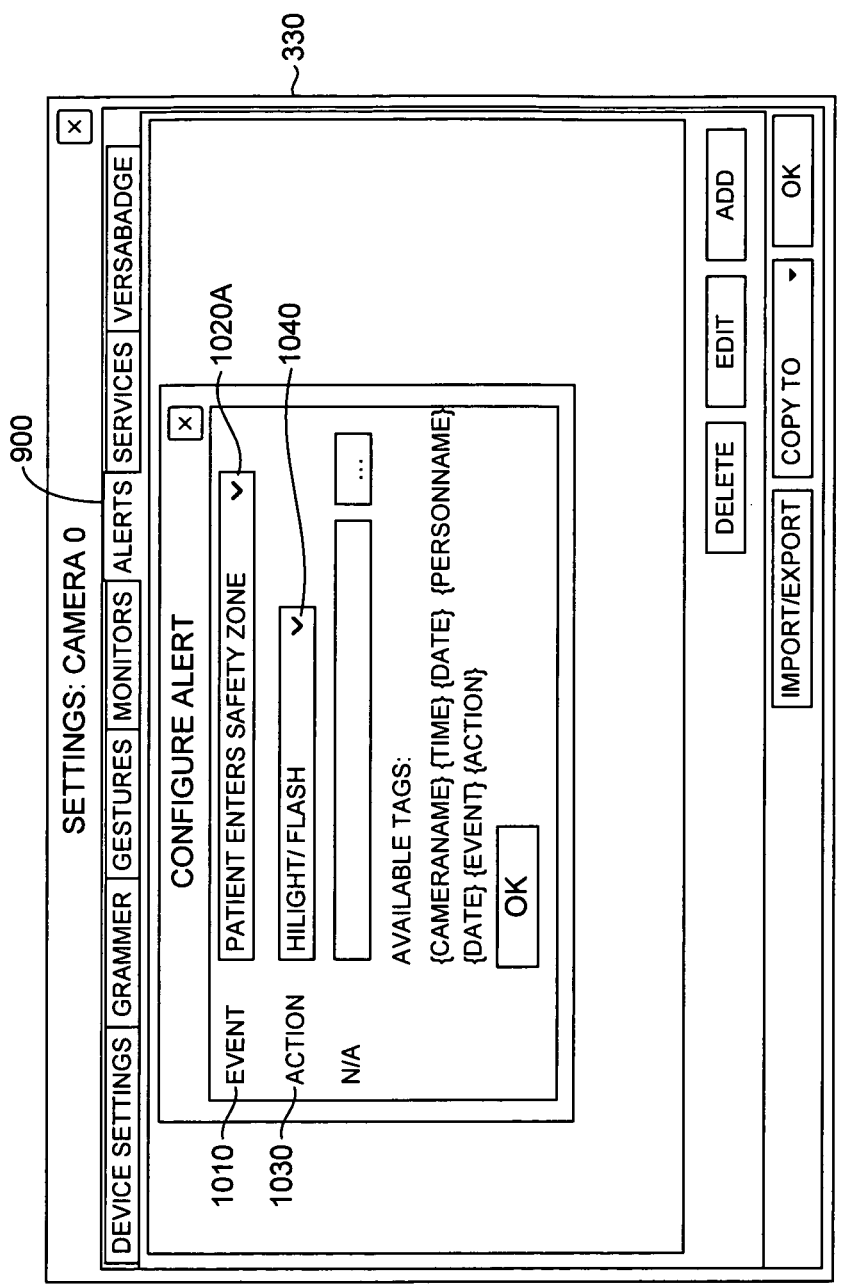
FIG. 12 is an exemplary interface for configuring a monitoring system.

FIG. 12 shows an alternative configuration screen in pop up menu 330 after selections have been made for event 1010 and action 1030. In the example of FIG. 12, the appearance of the display border, text, or other properties on centralized monitoring primary display 200, centralized monitoring alert display 210, or both will change (e.g., be highlighted or flash) if event 1020A occurs. In this case, the display appearance is configured to change if the patient enters the virtual safety zone, e.g., if the monitored individual places one or both hands in the virtual safety zone. The language used in the configuration menus is itself adaptable and configurable, and can be modified for a particular user group or environment. For example, hospital settings may refer to "patients" and use clinical terminology and/or healthcare industry shorthand. Monitoring services in home environments might refer to "clients" and use lay terminology. A particular institution or user group may have the option to configure the menu terminology when the system is initially installed, or as system maintenance and/or updates are undertaken, so that the menu terminology is familiar to the particular facility or user group adopting the system.

Figure 13:
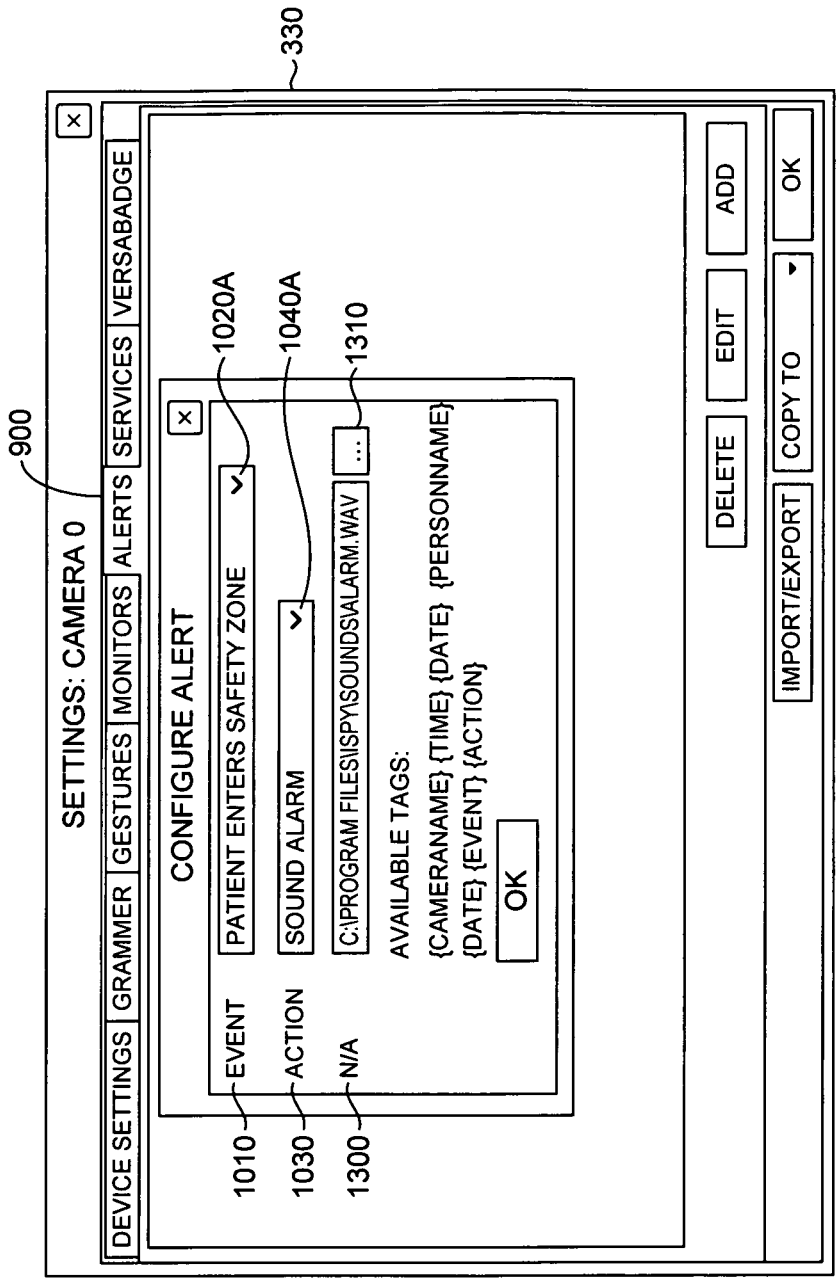
FIG. 13 is an exemplary interface for configuring a monitoring system.

FIG. 13 shows an exemplary configuration for a different alert. The configured event 1020A is still "PATIENT ENTERS SAFETY ZONE", but action 1030 has been configured to "SOUND ALARM" 1040A. On selecting "SOUND ALARM" 1040A, menu item 1300, labeled N/A (e.g., for Notification/Alarm) becomes active for user selection of configurable options. As shown in FIG. 13, the user has selected an alarm from a particular file. The sound file associated with the alarm might be played audibly on speakers in the room with monitored individual 100, to a paging or speaker system in a facility more broadly than the room with monitored individual 100 (e.g., audible at a central nursing station in a hospital unit, or in hallways or break rooms) or might be sent to a mobile or other device, e.g., attached to an e-mail or text message, or using an autodialing protocol that can deliver a message to a person who answers a phone call or to a voice mail account associated with a dialed number. Alternately, or additionally, the sound file may be played at the central monitoring station 130 to alert an attendant there.

Figure 14:
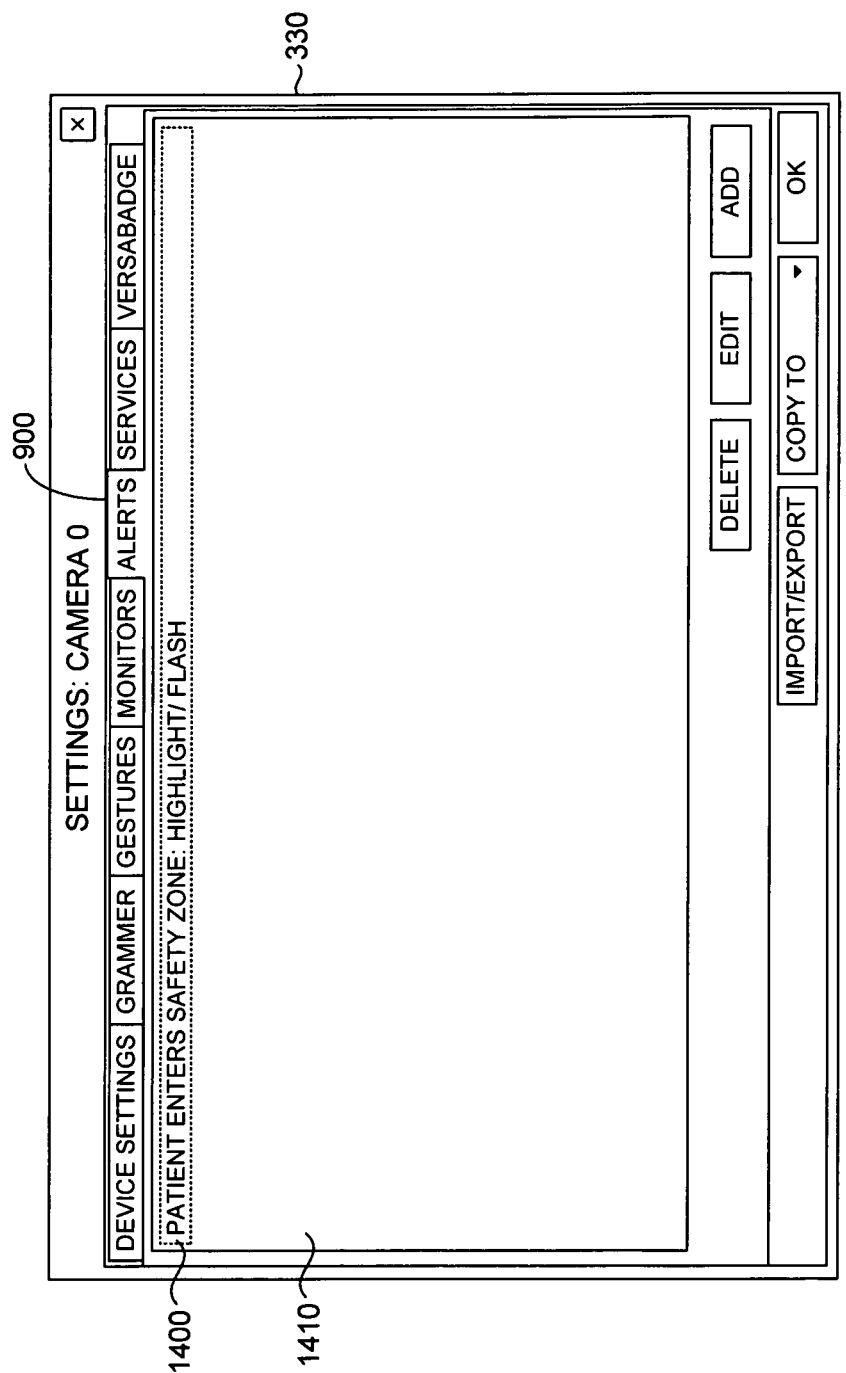
FIG. 14 is an exemplary interface for configuring a monitoring system.

FIG. 14 shows exemplary pop up menu 330 after an alert has been configured. On selecting alert tab 900, alert 1400, "PATIENT ENTERS SAFETY ZONE: HIGHLIGHT/FLASH" is shown. The description and/or level of detail displayed regarding alert 1400 can vary. If additional alerts were configured, they would appear in space 1410, preferably with descriptions of at least the event and the action for each alert. In this way, if multiple alerts are configured, it is easier to find a particular alert for later editing or deletion, if desired.

With reference to FIGS. 1 and 5, the computerized monitoring system 120 determines whether a monitored individual has placed one or both hands within the virtual safety zone 500 by creating a configurable three-dimensional zone or perimeter around any locations the caregiver determines that the monitored individual should not place their hand(s). The user may also define a predetermined length of time that the monitored individual's hand or hands must be in the virtual safety zone 500 before triggering an alarm. The 3D motion sensor 110 can be programmed to lock on the monitored individual 100, e.g., using a bed zone 510 as described below, and can send back to the computerized monitoring system 120 the 3D coordinates of the joints in the individual's body and a skeletal outline 320 of the monitored individual 100. The system is also able to recognize hand, body, and other movements and uses the information received from the 3D motion sensor 110 to determine if the monitored individual's hand(s) are in the virtual safety zone 500, how long the hand has been in that zone and what, if any, gestures the individual is making.

When the computerized virtual safety zone monitoring system 120 detects a monitored individual's hand(s) within the virtual safety zone 500, shown as 170 in FIG. 1, the computerized virtual safety monitoring system 120 may notify the computerized communication system 140, which may send an automated alert to the monitored individual 100 and/or caregiver(s) 160 that the monitored individual 100 has placed his or her hand(s) in the virtual safety zone 500. The detection may involve inferring the location of the monitored individual's hand(s), for example, based on the ends of the skeleton figure segments corresponding to the monitored individual's wrists. If facial tracking software is used, a hand or hands lifted to or near the face would obscure the facial tracking, i.e., one or more of the facial features being used for the facial tracking would be obscured by the hand or hands. As such, a partially lost or obscured signal could be used to determine that the monitored individual's hand(s) have entered the virtual safety zone 500. An electronic record of the entry into the virtual safety zone 500 may be made in database 150. The method of these alerts includes, but is not limited to, amplified speakers, microphones, lights, monitors, computer terminals, mobile phones and or other technologies to allow for the electronic communication to take place. The alert to the monitored individual 100 may include an audible or visual instruction, such as "please put your hands down," "please stop what you are doing," or "please wait, help is coming." For example, a paging system may be used to make an oral announcement in the monitored individual's room, or a text message may be displayed on a television or computer display in the monitored individual's room. The purpose of the alert may be to instruct the patient to discontinue activity consistent with disturbing medical equipment and/or temporary implants. The alerts may be available in two or more languages, allowing the system to provide instructions even if the monitored individual 100 does not speak the same primary language as the monitored individual's caregivers 160. The alert may be configured, using menus like those described above, to specify what language should be used for alerts to the monitored individual 100.

When an alert is triggered, the alert may be sent, at least initially, to the monitored individual 100, to give monitored individual 100 an opportunity to self-correct before alerting the central monitoring station 130 and/or caregivers 160. Alternately, central monitoring station 130 may be alerted with or even before the monitored individual, so that central monitoring station 130 can determine whether the entry into the virtual safety zone 500 is, in fact, problematic. The central monitoring station, or an attendant there, can do this by viewing the live video and/or audio feed from the 3D motion sensor(s), and determining whether the gestures or motions appear to be dangerous. The central monitoring station 130 attendant could then approve alert(s) to appropriate caregiver(s) 160 to intervene. In another alternative, one or more caregiver(s) 160 local to the monitored individual 100 can be alerted with or even before the monitored individual 100, so that the caregiver(s) 16 can assess what is happening in person. Or, the monitored individual 100, caregiver(s) 160 and the central monitoring station 130 could all be alerted at the same time. The priority and timing of alerts to different individuals or stations can be configured in accordance with the needs and desires of a particular facility, experience with a particular monitored individual or type of patient, or any other criterion of the system owner or user. This is true for initial alerts as well as continuing alerts (e.g., if a monitored individual receives an audible alert and does not remove his or her hands from the virtual safety zone) or repeated alerts (two or more distinct events where the monitored individual's hand or hands enter the virtual safety zone). The priority and timing of alerts to different individuals may be different for initial, continuing, and/or repeated alerts.

At step 180 in FIG. 1, the computerized virtual safety zone monitoring system 120 determines whether the monitored individual 100 has removed his or her hand(s) from the virtual safety zone 500. If the system detects that a monitored individual 100 has removed his or her hand(s) from the virtual safety zone 500, an electronic record can be made in database 150 and audible and/or visible alerts may be issued to the monitored individual 100 and/or caregiver(s) 160 to confirm compliance. The computerized virtual safety zone monitoring system 120 may continue to analyze incoming data from 3D motion sensor 110 for continued compliance.

Should the monitored individual 100 fail to remove his or her hand(s) from the virtual safety zone 500, an audible and/or visible alert can be given to the monitored individual 100 and/or caregiver(s) 160, notifying the monitored individual 100 and caregiver(s) 160 that the monitored individual 100 or caregiver 160 needs to take measures to remove the monitored individual's hand(s) from the virtual safety zone 500. The alert can be sent by the computerized communication system which can include, but is not limited to, a system of speakers, microphones lights, monitors, mobile phones and methods of communication including but not limited to voice, email, SMS messaging, video, phone calls or flashing lights. A second or subsequent alert to the monitored individual 100 maybe worded more strongly than the initial alert, using language like "Stop now. Help is coming." The computerized monitoring system 120 may monitor, using gesture recognition, location tracking, facial tracking, skeleton figure tracking, or other measures whether the monitored individual 100 has taken appropriate steps to remove his or her hand(s) from the virtual safety zone 500 based on the information received from the 3D motion sensor 110. Facial recognition could also be used, however, facial tracking is typically sufficient for the purpose of monitoring a virtual safety zone. An electronic record can be made in the database 150 and additional audible and/or visible alerts can be issued to the monitored individual 100 and/or caregiver(s) 160 until the monitored individual 100 removes his or her hand(s) from the virtual safety zone 500. Captured video can also be stored and/or reviewed by the computerized monitoring system 120 when the system makes its determination.

If the monitored individual 100 places his or her hand(s) in the virtual safety zone 500, notification may be given to the caregivers 160 or other designated persons. Notification of caregivers can be made through phone call, text messaging, speakerphone systems, email, or other electronic means of communication. The system database 150 may also be updated to reflect actions taken.

FIG. 2 shows the workflow for centralized monitoring and alerting regarding whether a monitored individual's hand(s) have encroached into a virtual safety zone through the use of 3D motion sensors 110. One or more 3D motion sensors, shown as 110A, 110B, and 110C in FIG. 2, are installed in and/or just outside a monitored individual's room, home, hospital room, or other place of temporary or permanent residence and connected to computerized monitoring and communication systems as shown in FIG. 1. Video and/or audio data for a monitored individual, such as individuals 100A, 100B, and 100C, is collected by 3D motion sensors 110A, 110B, and 110C, respectively. The video and/or audio data is transferred by the 3D motion sensors 110A, 110B, and 110C to computerized monitoring and communication systems 120A, 120B, and 120C, respectively. Video, audio and alert data is sent by the computerized monitoring and communication systems 120A, 120B, and 120C to a centralized monitoring station 130 where the data is aggregated for various monitored individuals. The computerized monitoring systems 120A, 120B, and 120C receive the raw data from the 3D motion sensors 110A, 110B, and 110C, run the skeletal recognition, facial tracking, and/or gesture recognition algorithms, and then send the audio, video and alert data to the centralized monitoring station 130. The centralized monitoring station 130 receives and displays this data from one or more sensors/computerized monitoring systems. Similar to a grid of cameras being watched on a screen (i.e. where a plurality of camera feeds are viewed on a single screen), the centralized monitoring station aggregates the various video feeds, as it receives and displays information from multiple cameras. Preferably, the centralized monitoring station 130 receives data at all times, e.g., continuously, from the 3D motion sensors 110A, 110B, and 110C, typically via computerized monitoring and communication systems 120A, 120B, and 120C, to allow the various individuals to be constantly monitored at the centralized monitoring station 130 regardless of whether or not a breach of the virtual safety zone 500 has been detected.

All video, audio and/or alert feeds received by the centralized monitoring station 130 can be displayed on the centralized monitoring primary display 200. Alternatively, multiple centralized monitoring primary displays can be utilized based on the quantity of rooms to be monitored at a given time.

When the centralized monitoring station 130 receives an alert from any of the computerized monitoring and communication systems 120A, 120B, 120C, indicating that a monitored individual 100 has placed his or her hand(s) in the virtual safety zone 500, the video, audio and/or alert information for that particular individual is displayed on the Centralized Monitoring Alert Display 210. An alert can be represented in one or more different types of physical configurations. It can be a visual queue on screen at the centralized monitoring station 130 such as the specific camera view flashing or being highlighted in a color to draw attention to that display among others. It can be an audible sound (voice or alarm type sound) at the centralized monitoring station 130, an audible sound at the computerized monitoring system 120 attached to the 3D motion sensor 110, a text message, an email, turning on a light or even running a program on a computer. Should the centralized monitoring station 130 receive alerts from more than one of the computerized monitoring and communication systems 120A, 120B, 120C, indicating that a monitored individual 100 has placed his or her hand(s) in the virtual safety zone 500, the centralized monitoring alert display 210 will display the video, audio and/or alerting information from all such instances at the same time. If no alert is received by the centralized monitoring station 130, nothing is displayed on the centralized monitoring alert display 210. Preferably, all monitored individual rooms can be displayed and visible on the central monitoring primary display 200 whether alerting or not. When an alert is generated, attention can be drawn to the particular camera and a duplicative display of the alerting camera can be displayed on a second separate computer monitor, e.g., the centralized monitoring alert display 210.

An electronic record of any alerts received by the centralized monitoring station 130 can be stored in a database 150.

The various components described can be in electrical, wired and/or wireless communication with each other. The various computerized systems and processors as described herein may include, individually or collectively, and without limitation, a processing unit, internal system memory, and a suitable system bus for coupling various system components, including database 150, with a control server. Computerized monitoring system 120 and/or centralized monitoring station 130 may provide control server structure. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus.

The computerized systems typically include therein, or have access to, a variety of computer-readable media, for instance, database 150. Computer-readable media can be any available media that may be accessed by the computerized system, and includes volatile and nonvolatile media, as well as removable and non-removable media. By way of example, and not limitation, computer-readable media may include computer-storage media and communication media. Computer-storage media may include, without limitation, volatile and nonvolatile media, as well as removable and non-removable media implemented in any method or technology for storage of information, such as computer readable instructions, data structures, program modules, or other data. In this regard, computer-storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by one or more of the computerized systems. Computer-storage media excludes signals per se.

Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media. The computer-storage media discussed above, including database 150, provide storage of computer readable instructions, data structures, program modules, and other data for the computerized systems.

The computerized systems may operate in a computer network using logical connections to one or more remote computers. Remote computers may be located at a variety of locations, for example, but not limited to, hospitals and other inpatient settings, veterinary environments, ambulatory settings, medical billing and financial offices, hospital administration settings, home health care environments, payer offices (e.g., insurance companies), home health care agencies, clinicians' offices and the clinician's home or the patient's own home or over the Internet. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers may also be physically located in non-traditional medical care environments so that the entire health care community may be capable of integration on the network. The remote computers may be personal computers, servers, routers, network PCs, peer devices, other common network nodes, or the like, and may include some or all of the elements described above in relation to the control server. The devices can be personal digital assistants or other like devices.

Exemplary computer networks may include, without limitation, local area networks (LANs) and/or wide area networks (WANs). Such networking environments are commonplace in offices, enterprise-wide computer networks, intranets, and the Internet. When utilized in a WAN networking environment, the control server may include a modem or other means for establishing communications over the WAN, such as the Internet. In a networked environment, program modules or portions thereof may be stored in the control server, in the database 150, or on any of the remote computers. For example, and not by way of limitation, various application programs may reside on the memory associated with any one or more of the remote computers. It will be appreciated by those of ordinary skill in the art that the network connections shown are exemplary and other means of establishing a communications link between the computers may be utilized.

In operation, a user may enter commands and information into the computerized system(s) using input devices, such as a keyboard, a pointing device (commonly referred to as a mouse), a trackball, or a touch pad. Other input devices may include, without limitation, microphones, satellite dishes, scanners, or the like. In addition to or in lieu of a monitor, the computerized systems may include other peripheral output devices, such as speakers and a printer.

Many other internal components of the computerized system hardware are not shown because such components and their interconnection are well known. Accordingly, additional details concerning the internal construction of the computers that make up the computerized systems are not further disclosed herein.

Methods and systems of embodiments of the present disclosure may be implemented in a WINDOWS or LINUX operating system, operating in conjunction with an Internet-based delivery system, however, one of ordinary skill in the art will recognize that the described methods and systems can be implemented in any system suitable for supporting the disclosed processing and communications. As contemplated by the language above, the methods and systems of embodiments of the present invention may also be implemented on a stand-alone desktop, personal computer, cellular phone, smart phone, tablet computer, PDA, or any other computing device used in a healthcare environment or any of a number of other locations.

EXAMPLE 1

Configuring Zones

The bed zone 510 and virtual safety zone 500 for a given 3D motion sensor 110 can be configured. To begin, the user hovers over the 3D motion sensor video window with the cursor, then right-clicks, select plugins and then select configure plug-ins. A window will pop up showing the 3D motion sensors' feed.

The user selects the icon(s) for the type of zone they wish to draw. In this non-limiting example, a bed zone 510 and a virtual safety zone 500 can be selected.

As non-limiting examples, the following icons can appear on the screen for selection:
Safety Zone
Bed Zone
Auto Bed Zone (Select Patient)
Auto Bed Zone (Auto-select)

Saved Zones

Clear All

To place a zone, the user clicks on the screen where the user would like to start the zone. Then, the cursor is moved to the corner point and clicked again. The user continues selecting additional points until the zone is drawn to the user's satisfaction. Preferably, the user clicks on the round end point of the beginning of the zone to complete the zone. Upon completion the zone appears and has a depth range box preferably in the middle.

The user can adjust the depth range for any given zone. By double clicking on the depth range box, or by other user selection method, an Edit Depth window can appear. The user can enter in the depth ranges (for example, in millimeters (mm)) and then the user can click the Save button or icon when done to store the entered values. Although this example uses millimeters for depth range values, depth ranges could be entered in any desired unit of measurement including, but not limited to, centimeters, meters, inches, feet and yards.

If there are any other types of zones to draw for the particular sensor, the above steps can be repeated to place the next zone and the depth setting can be adjusted for each if necessary or desired. Additionally, all zones can be cleared by clicking on or otherwise selecting the Clear All icon preferably located in the toolbar.

Once all zones/wires are configured; the window can be closed to finish or an option to save the zone configuration for later use can be provided and selected.

To access the main settings window, the user can click on the Settings menu and select the Main Settings listing from the drop-down list. Alternately, the user can click on the Gear icon in the toolbar to access the main settings window or utilize a designated keyboard shortcut.

EXAMPLE 2

Configuring an Alert

For one non-limiting way to configure a new Alert, the user can select an Alerts tab and then click on or otherwise select the Add button, which can result in the Configure Alert box to appear on the screen.

Under the Event field in the Configure box, the user can select the event from the drop down list that they wish to alert on.

Once the Event type is selected, under the Action field, the user can select the Action he or she wishes to have the system perform when the selected Event is detected.

For certain Actions an additional field may need to be completed to finish the Action. If the field is required, it can appear below the Action dropdown. If no further fields are required, the Configure Alert box can display N/A or just be blank.

Once all of the settings are selected the user clicks on or otherwise selects the OK button (or similar function button) which saves the new Alert.

The new Alert can now be listed in the Alerts tab window. To edit an existing Alert, the user first clicks on or otherwise selects the Alert and then selects the Edit button. To delete an Alert, the user can first highlight the Alert and then click on the Delete button.

To add more Alerts, the user clicks or selects the Add button and repeats steps 4-6. When finished, the user clicks on or otherwise selects the bottom corner OK button to save and close the window.

Automatically detecting and providing alerts to a monitored individual and/or caregivers when a monitored individual enters a virtual safety zone, may reduce incidences of HAIs by lowering the risk of improper disturbance and/or removal of medical equipment; increase the survival rate for individuals who are susceptible to HAIs; reduce costs for hospitalization and medical care related to HAIs; reduce costs for hospitalization and medical care related to re-insertion of improperly removed medical equipment; or reduce injury and deaths of monitored individuals who have improperly removed medical equipment.

From the foregoing, it will be seen that this disclosure is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

What is claimed is:

1. A method for detecting when a monitored individual has moved one or both of his or her hands within a virtual safety zone, the method comprising, at a computerized monitoring system:

receiving one or more selections for configuring a virtual safety zone representing an area where an individual to be monitored should not place his or her hands;

accessing one or more 3D motion sensors to capture live video data from the virtual safety zone;

receiving the video data from the one or more 3D motion sensors;

determining that one or more hands of the individual to be monitored are within the virtual safety zone;

determining that an amount of time the one or more hands are within the virtual safety zone meets or exceeds a predetermined period of time; and upon determining that the one or more hands of the individual are within the virtual safety zone for at least the predetermined period of time, electronically transmitting an alert to at least one of the monitored individual, one or more caregivers, and a centralized monitoring station.

2. The method of claim 1, further comprising forwarding a live video feed of the virtual safety zone received from the one or more 3D motion sensors to a centralized video monitoring station for display after it has been determined that the one or more hands of the monitored individual is within the virtual safety zone for the predetermined period of time.

3. The method of claim 1 further comprising continuously forwarding a live video feed of the virtual safety zone received from the one or more 3D motion sensors to a centralized video monitoring station for display, the centralized video monitoring station being remotely located from a room in which the individual is monitored.

4. The method of claim 1 further comprising continuously forwarding a live video feed of the virtual safety zone received from the one or more 3D motion sensors to a centralized video monitoring station for display after it has been determined that the one or more hands of the monitored individual is within the virtual safety zone.

5. The method of claim 1 further comprising updating a database in communication with the computerized monitoring system regarding the determination that at least one hand of the monitored individual was within the virtual safety zone.

6. The method of claim 1 further comprising notifying a designated caregiver by electronic message regarding the determination that at least one hand of the monitored individual was within the virtual safety zone.

7. The method of claim 1, wherein the virtual safety zone encompasses at least part of the monitored individual's face.

8. The method of claim 7, wherein the determining that one or more hands of the monitored individual are within the virtual safety zone comprises using facial tracking to monitor the virtual safety zone and detecting at least a partially lost facial tracking signal for the individual's face.

9. A system for determining whether a monitored individual has placed one or both hands in a virtual safety zone, the system comprising:
   one or more 3D motion sensors co-located with a monitored individual;
   a computerized monitoring system configured to:
      receive data from the one or more 3D motion sensors;
      identify a position of one or more hands of the monitored individual;
      determine whether the one or more hands of the monitored individual have entered a virtual safety zone;
      determine that the one or more hands are within the virtual safety zone for at least a predetermined period of time; and
      upon determining that the one or more hands of the individual are within the virtual safety zone for at least the predetermined period of time, transmit, to a computerized communication system, a determination that the one or more hands are within the virtual safety zone;
   the computerized communication system configured to:
      receive, from the computerized monitoring system, the determination that the one or more hands of the individual are within the virtual safety zone; and
      send an alert of the one or more hands being in the virtual safety zone to at least one designated recipient.

10. The system of claim 9, wherein the computerized monitoring system is further configured to actuate a timer upon determining that the one or more hands of the individual have entered the virtual safety zone.

11. The system of claim 9, wherein the designated recipient includes one or more of a caregiver, the monitored individual, an alternate caregiver, and a supervisor.

12. The system of claim 9, wherein the alert comprises an audible instruction to the monitored individual.

13. The system of claim 12, wherein the computerized communication system is further configured to send an alert to one or more caregivers prior to the audible instruction being sent to the monitored individual.

14. The system of claim 9, further comprising a database for logging events related to the entry of the one or more hands of the monitored individual into the virtual safety zone.

15. The system of claim 14, wherein the computerized communication system is further configured to log entries for events related to the entry of the one or more hands of the monitored individual into the virtual safety zone and related alerts.

16. Non-transitory computer-readable storage media having stored thereon executable instructions which, when executed by a computer, cause the computer to:
   receive visual data from one or more 3D motion sensors;
   identify a monitored individual's location from the visual data;
   establish a virtual safety zone at least partially overlapping the monitored individual's location;
   identify one or more hands of the monitored individual from the visual data;
   determine, using the visual data, whether the one or more hands of the monitored individual enter the virtual safety zone;
   time the duration for which the one or more hands of the monitored individual remain in the virtual safety zone;
   determine that the duration for which the one or more hands of the monitored individual remain in the virtual safety zone meets or exceeds a predetermined period of time; and
   issue an alert upon determining the duration meets or exceeds the predetermined period of time.

17. The media of claim 16, wherein to establish a virtual safety zone at least partially overlapping the monitored individual location, the instructions further cause the computer to present a human-readable visual image of the monitored individual's location to a display device, and to accept user input to define the virtual safety zone.

18. The media of claim 16, wherein the instructions further cause the computer to log the alert in a database.

19. The media of claim 16, wherein the monitored individual is identified using one or more biometric identifiers, and the virtual safety zone is established after the monitored individual is identified.

* * * * *

UNITED STATES PATENT AND TRADEMARK OFFICE
CERTIFICATE OF CORRECTION

PATENT NO. : 10,090,068 B2
APPLICATION NO. : 14/757593
DATED : October 2, 2018
INVENTOR(S) : Neil Kusens et al.

Page 1 of 1

It is certified that error appears in the above-identified patent and that said Letters Patent is hereby corrected as shown below:

In the Specification

Column 1, Line 32: Please remove "condition," and replace with --condition.--.
Column 10, Line 8: Please remove "and or" and replace with --and/or--.
Column 15, Line 28: Please remove "configured;" and replace with --configured,--.

Signed and Sealed this
Twenty-seventh Day of November, 2018

Andrei Iancu
*Director of the United States Patent and Trademark Office*